(12) United States Patent
Gianotti et al.

(10) Patent No.: US 10,898,696 B2
(45) Date of Patent: Jan. 26, 2021

(54) HYDRAULICALLY ACTUATED AND FUNCTIONALLY INTEGRATABLE CATHETER SYSTEM FOR TREATING VASCULAR AND NON-VASCULAR DISEASES AND RELATED METHODS

(71) Applicant: CTI Vascular AG, Neuhausen (CH)

(72) Inventors: Marc Gianotti, Wiesendangen (CH); Ulf Fritz, Tengen (DE); Dragana Gajic, Schaffhausen (CH)

(73) Assignee: CTI Vascular AG, Neuhausen (CH)

( * ) Notice: Subject to any disclaimer, the term of this patent is extended or adjusted under 35 U.S.C. 154(b) by 292 days.

(21) Appl. No.: 15/744,012

(22) PCT Filed: Jan. 11, 2016

(86) PCT No.: PCT/EP2016/050376
§ 371 (c)(1),
(2) Date: Jan. 11, 2018

(87) PCT Pub. No.: WO2017/008918
PCT Pub. Date: Jan. 19, 2017

(65) Prior Publication Data
US 2018/0200489 A1 Jul. 19, 2018

Related U.S. Application Data

(60) Provisional application No. 62/191,515, filed on Jul. 13, 2015.

(51) Int. Cl.
*A61M 25/10* (2013.01)
*A61M 25/00* (2006.01)
*A61M 25/01* (2006.01)

(52) U.S. Cl.
CPC ...... *A61M 25/104* (2013.01); *A61M 25/0097* (2013.01); *A61M 25/0136* (2013.01);
(Continued)

(58) Field of Classification Search
CPC .......... A61M 25/0097; A61M 25/0136; A61M 25/0155; A61M 2025/1068; A61M 2025/0004; A61M 2025/0681
See application file for complete search history.

(56) References Cited

U.S. PATENT DOCUMENTS 4,323,071 A * 4/1982 Simpson ........... A61M 25/0054
128/DIG. 18

* cited by examiner

*Primary Examiner* — Sarah A Simpson
(74) *Attorney, Agent, or Firm* — Olympic Patent Works PLLC

(57) ABSTRACT

A comprehensive multi-functional device platform that can be variably configured by clinician operators for patient-specific anatomies and clinical situations for treating complex and total occlusions is provided. This device platform enables physicians of any skill level to effectively treat the most challenging and complex lesions/occlusions more conveniently in less time. The Functionally Integratable Catheter System ("FICS System") represents a system of "functional units" that can be configured together to operate synergistically, and comprises at least five main "functional units," including: (a) FICS Support Catheter; (b) FICS Dilator; (c) FICS PTA Catheter; (d) FICS Lock-Grip Handle; and (e) FICS Steering Hub. Each "functional unit" can be provided in a pre-assembled form by the manufacturer, intended to be configured into variable combinations by clinician operators.

21 Claims, 15 Drawing Sheets

(52) U.S. Cl.
CPC . *A61M 25/0155* (2013.01); *A61M 2025/0004* (2013.01); *A61M 2025/1068* (2013.01)

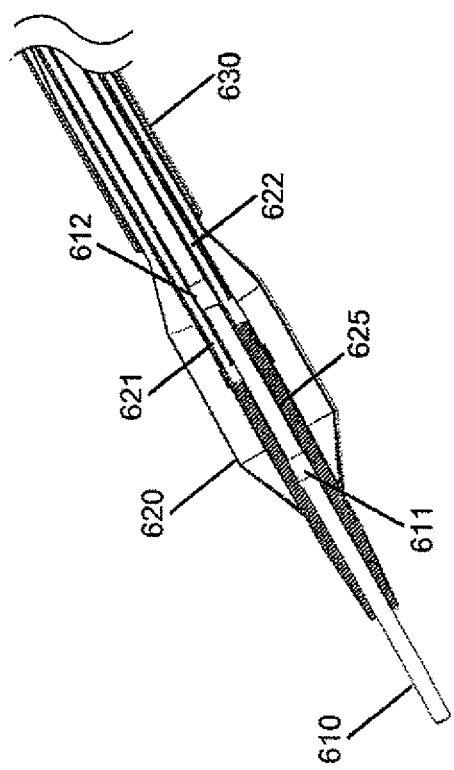
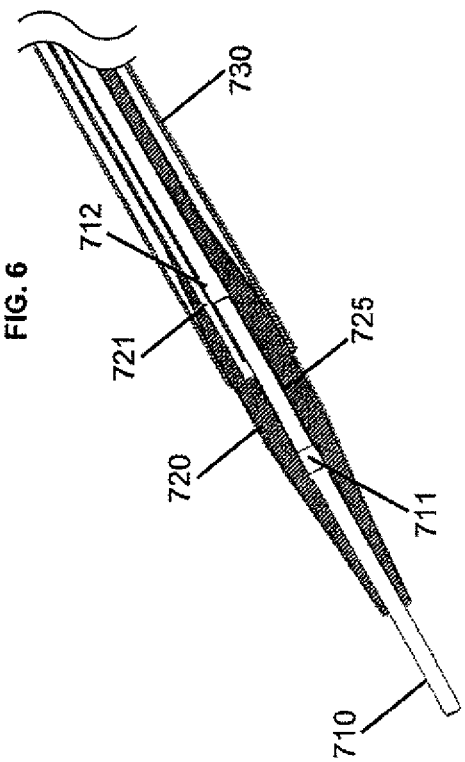
FIG. 6
FIG. 7

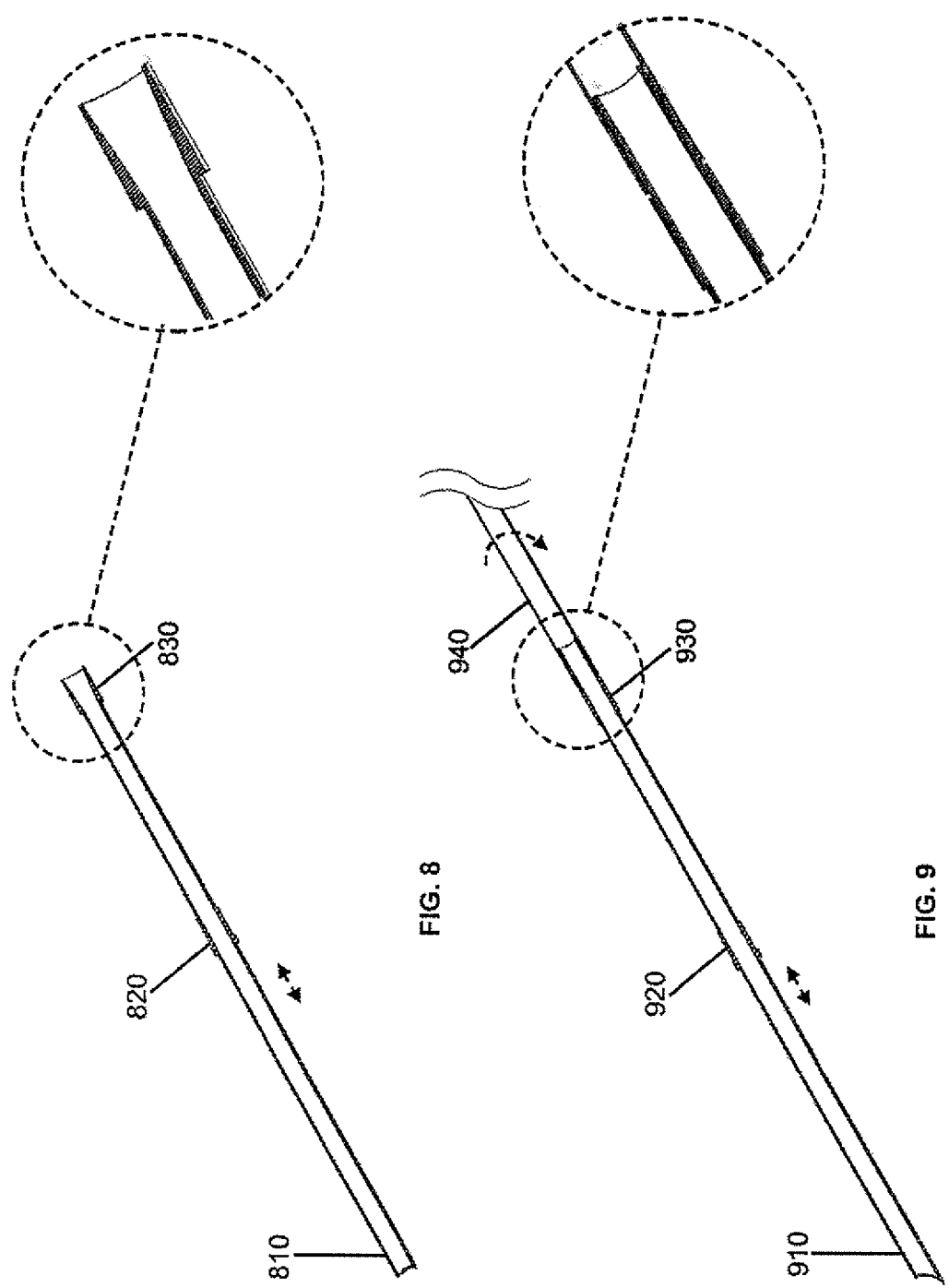

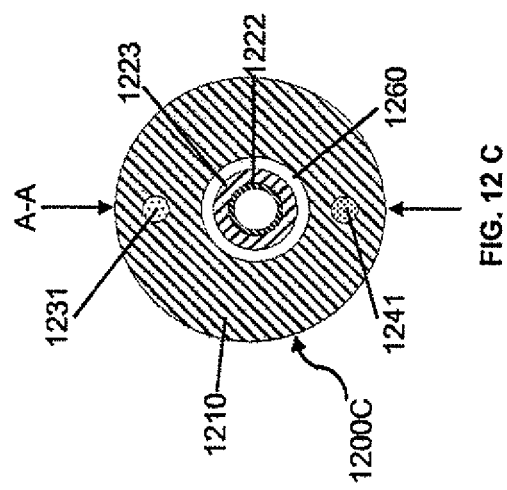
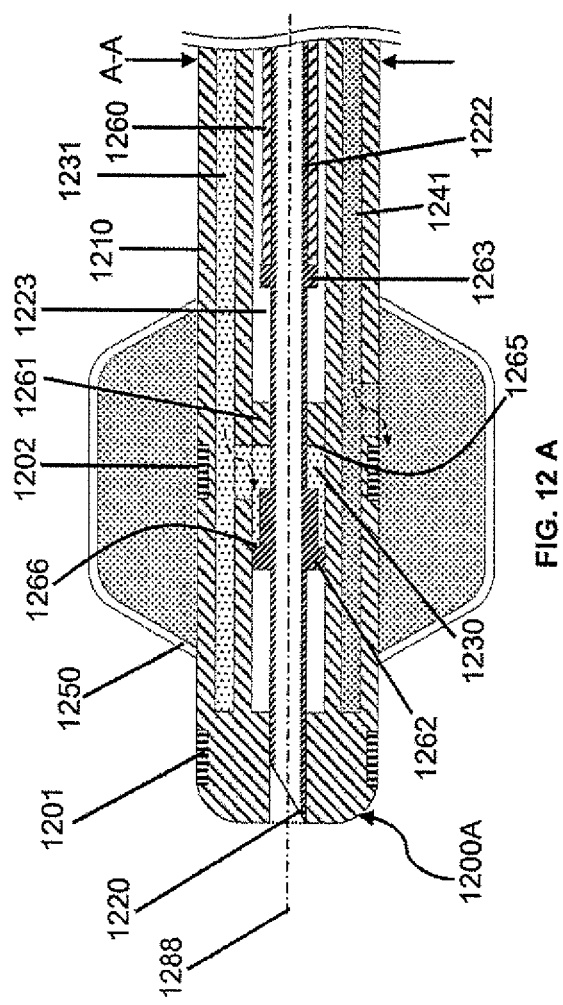
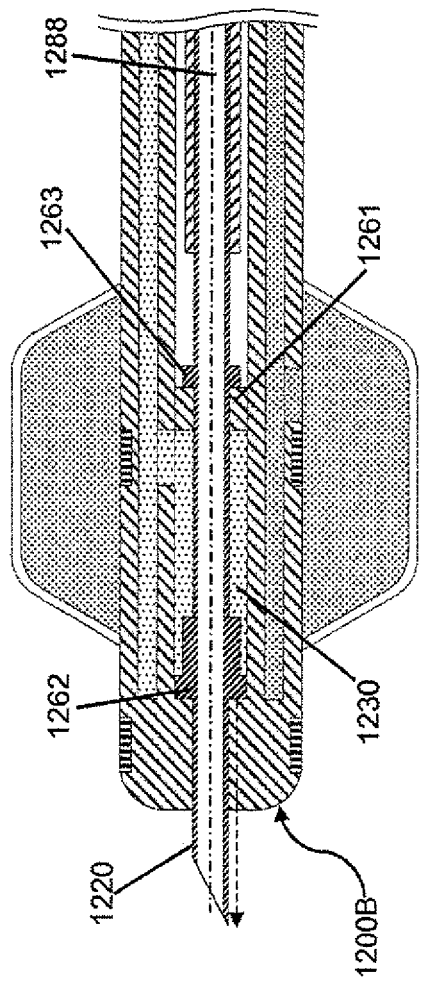

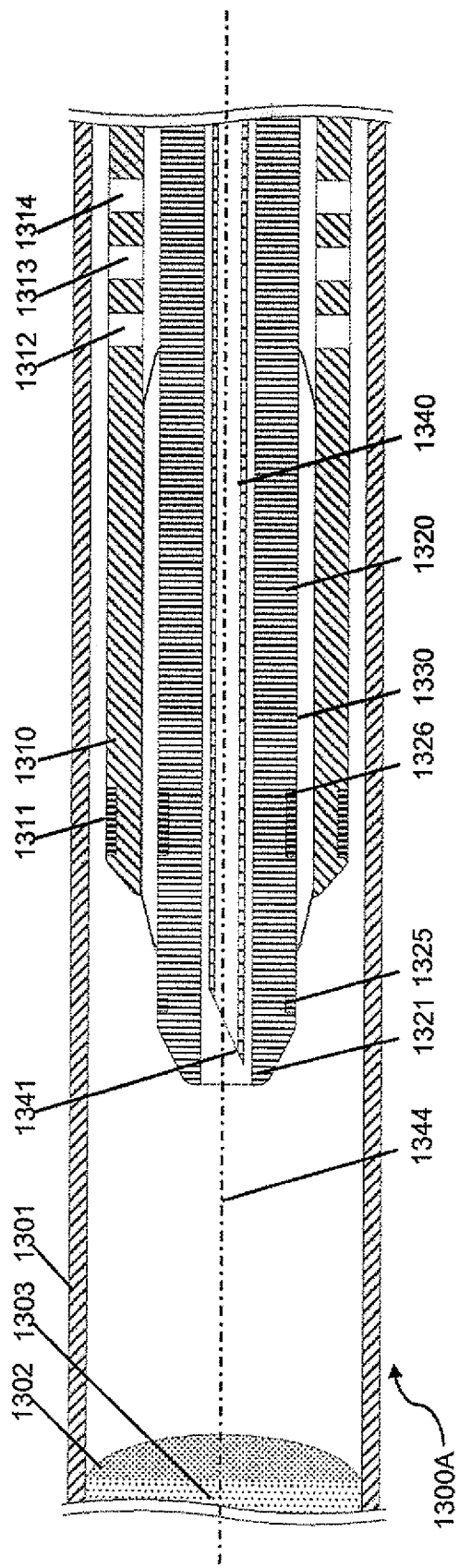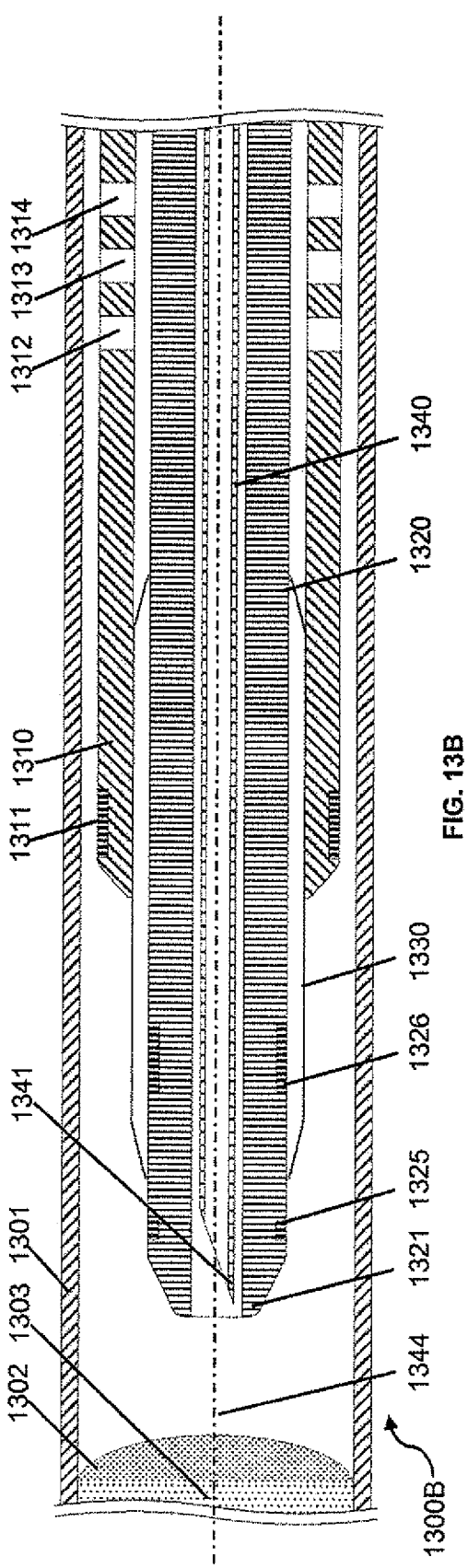
FIG. 13A
FIG. 13B

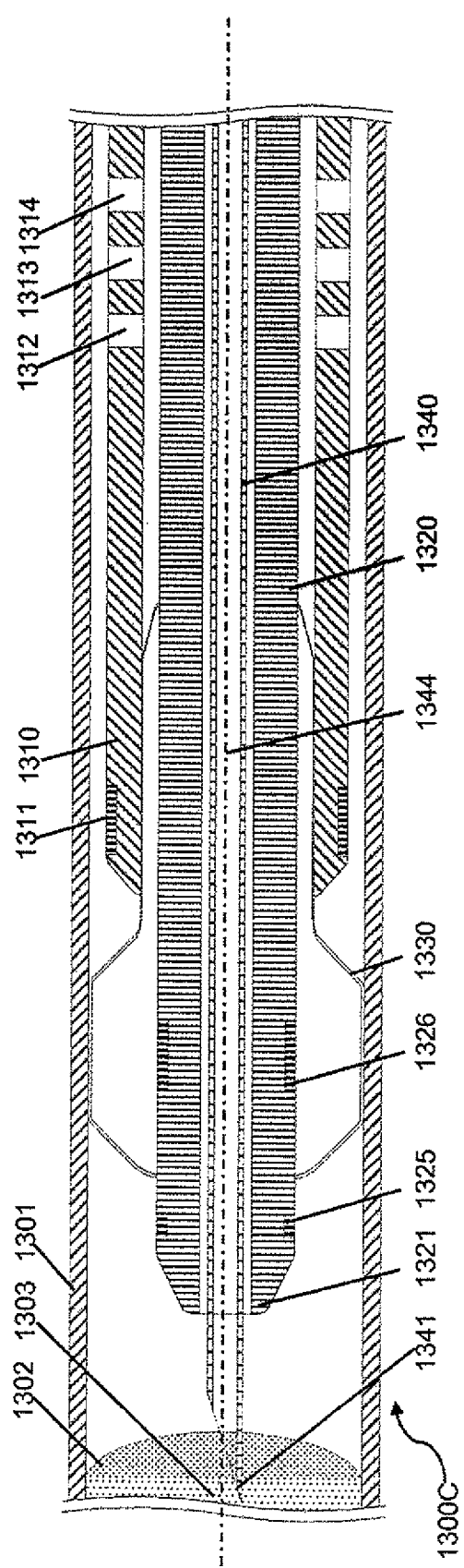
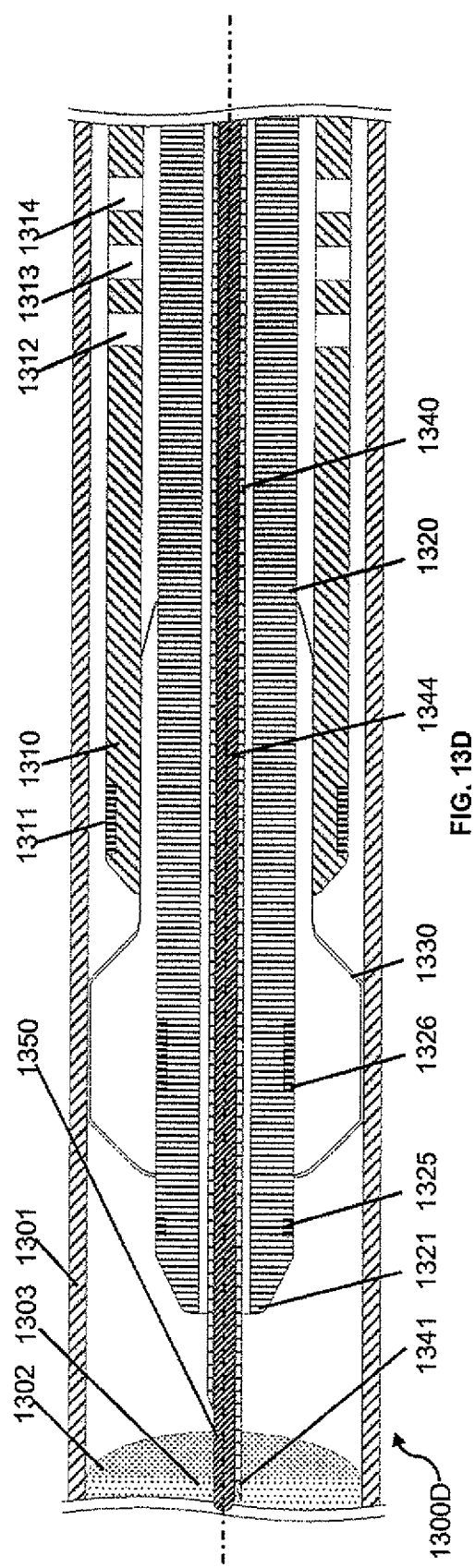
FIG. 13C
FIG. 13D

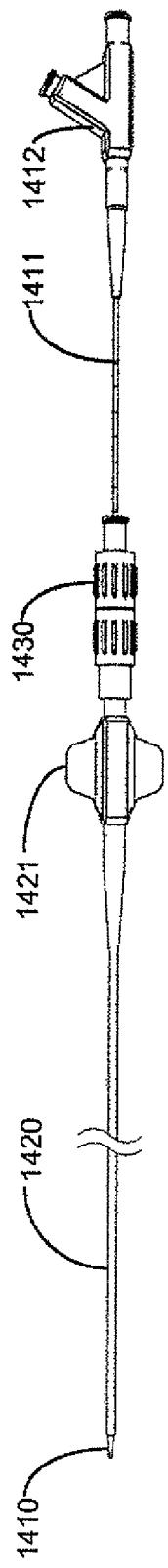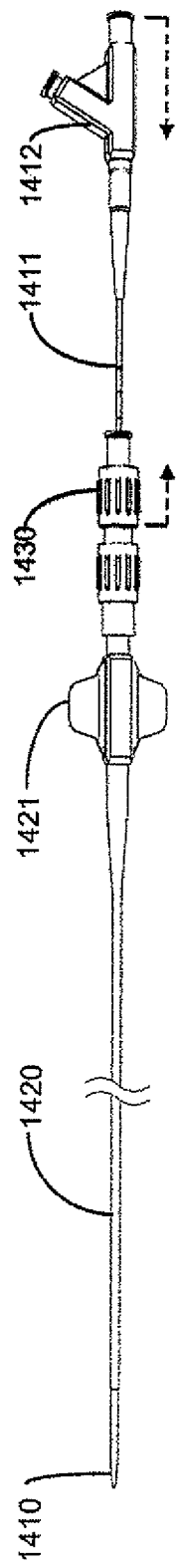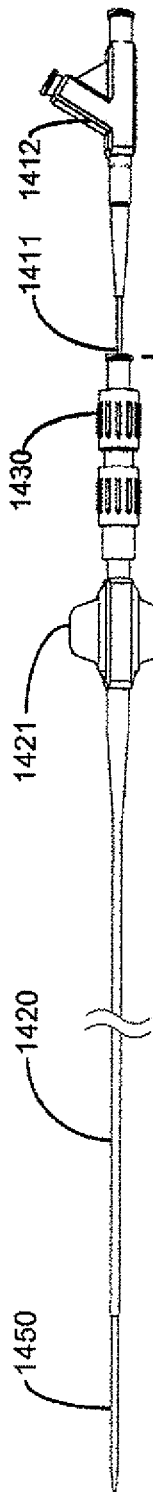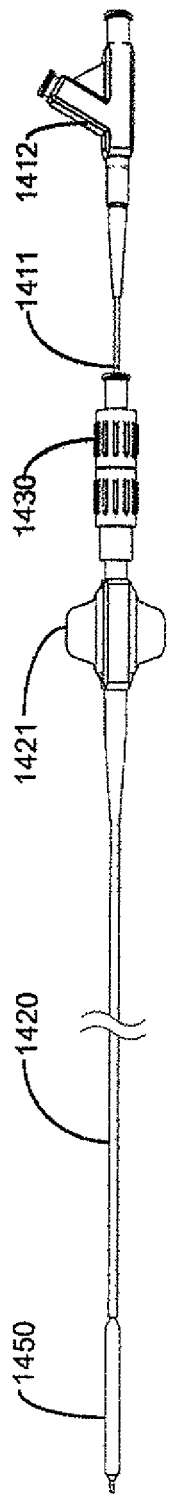
FIG. 14 A
FIG. 14 B
FIG. 14 C
FIG. 14 D

HYDRAULICALLY ACTUATED AND FUNCTIONALLY INTEGRATABLE CATHETER SYSTEM FOR TREATING VASCULAR AND NON-VASCULAR DISEASES AND RELATED METHODS

CROSS-REFERENCE TO RELATED APPLICATIONS

This application claims priority to PCT Application No. PCT/EP2016/050376, filed Jan. 11, 2016, which claims the benefit of U.S. provisional application 62/191,515, filed on Jul. 13, 2015, the content of which is hereby incorporated by reference in entirety.

TECHNICAL FIELD

The present disclosure is related to a hydraulically enabled functionally integratable catheter system ("FICS System"), comprising a support catheter, a dilator, a balloon catheter, a lock-grip handle, and a steering hub, which can be functionally and dimensionally configured for their in viva assembly, in various configurations, by physicians, for the treatment of vascular and non-vascular conditions/diseases, including complex lesions and chronic total occlusions (CTO).

BACKGROUND OF THE INVENTION

Atherosclerosis is a specific type of vascular disease, manifested by the accumulation of degenerative material along the lumen of blood vessel walls. Atherosclerosis is acknowledged as one of the major leading causes of death and morbidity in the Western world. Atherosclerosis can be asymptomatical at the early stages without noticeable discomfort or pain. However, if the disease progresses unabated, the affected vessels can develop plaques exhibiting variable textures resulting in increasingly complex lesion(s), for which the size and the severity can cause (a) successive reduction in lumen diameter; (b) restriction in blood flow; and (c) impairment in vessel flexibility in direct response to substantial thickening and hardening of blood vessels attributed to the cumulative formation of plaques/lesions along affected vessels. A chronic plaque build-up (i.e., composed of mixtures of fatty, fibrous and/or calcified tissue matters) can eventually reach a state, where blood flow becomes entirely insufficient to support the perfusion of local tissues, leading to a condition known as "chronic total occlusion" (CTO). CTO recanalization treatments to re-open obstructed vessels can present a number of inherent technical challenges to engineers who design medical devices that enable CTO recanalization and to physicians who depend on the use of clinically approved medical devices provided by device manufacturers. Ideally, the practicing physicians would have access to the most effective therapeutic medical devices in order to penetrate inherently challenging CTO situations of any size and severity, regardless of patient-specific anatomical variations. Currently, the interventional instruments available to physicians may be adequate; however, some procedural inefficiencies and limitations continue to exist due to the inherent limitations in product design and patient anatomical complexities. There is an unmet need to provide improved medical devices for treating complex lesions and chronic total occlusions (CTO) caused by atherosclerotic diseases.

SUMMARY

The present disclosure provides a comprehensive multi-functional device platform for treating complex lesions, including total occlusions, enabling physicians of any skill level to effectively treat the most challenging and complex vessel pathologies more conveniently in less time. The present disclosure provides a Functionally Integratable Catheter System ("FICS") representing a system for "functional units" that can be assembled together, by clinical operators, as therapeutic-specific "configurations" that can operate synergistically. FICS comprises at least five main "functional units," including: (a) FICS Support Catheter; (b) FICS Dilator; (c) FICS PTA Catheter; (d) FICS Lock-Grip Handle; and (e) FICS Steering Hub. Each "functional unit" can be provided in a pre-assembled form by the manufacturer, optionally pre-packaged as a device tray that includes the functional units (a)-(e), intended to be selectively assembled into variable configurations by clinical operators. The configurational adaptability of the FICS platform enables the physician to efficiently address multiple procedural aspects of the clinical intervention process (e.g., lesion access, lesion penetration, guide wire negotiation, lesion recanalization and dilation) by providing in situ treatment options (intraluminal and/or extraluminal recanalization), and enables multi-stage, patient-customized treatments of complex lesions in vivo (lesion-length-selective, multi-stage angioplasty treatment). In particular, the FICS System can be selectively configured by a clinical operator in order to recanalize extended complex lesions by providing a length-adaptable balloon member capable of matching the length of a target lesion ("lesion-length adjustability") conferred by the "FICS LLS PTA configuration" disclosed herein. A visual map of the various "functional units" and "functional subunits" that can be selectively combined by a clinical operator for constructing specific "FICS configurations" most effective for treating a broad range of complex lesions and CTOs is provided in a flow-chart diagram in FIG. 17.

Various embodiments are directed to the FICS components that can be pre-assembled into various "functional units" by the manufacturer. Various embodiments are directed to the specific "configurations" that can be assembled together by clinical operators involving the selective combination of different FICS "functional units" that can be configured specifically to be most effective in treating a broad range of complex lesions and CTOs. Various embodiments are directed to methods for manufacturing the FICS "functional units" and "functional subunits" disclosed herein. Various embodiments are directed to the methods for treating vascular and/or non-vascular diseases utilizing one or more disclosed "FICS configurations" for facilitating several therapeutic functionalities, including improved: (a) guide-wire negotiations; (b) lesion penetrations; (c) lesion recanalizations; (d) lesion dilations; and (e) vessel-lumen restorations.

BRIEF DESCRIPTION OF THE DRAWINGS

FIG. 2 illustrates two alternative FICS Dilators adatable for intraluminal or extraluminal CTO recanalization.

FIG. 6 illustrates a cross-sectional view of a hydraulically actuated "CTO Penetration Tip" with anchoring and/or centering functionality that can be incorporated into the distal tip of a FICS Dilator, as an embodiment.

FIG. 7 illustrates a cross-sectional view of a hydraulically actuated "CTO Penetration Tip" without anchoring and/or centering functionality that can be incorporated into the distal tip of a FICS Dilator, as an embodiment.

FIG. 8 illustrates a lateral view of a hydraulically actuated, non-steerable distal tip portion of a FICS Dilator, capable of translational movement along the longitudinal axis, as an embodiment.

FIG. 9 illustrates a lateral view of a hydraulically actuated, steerable distal tip portion of a FICS Dilator, capable of translational movement and rotational movement about the longitudinal axis, as an embodiment.

FIGS. 10 A-B provides exemplary dilator tip designs for facilitating intraluminal and extraluminal recanalization.

FIG. 12 illustrates a cross-sectional view of a hydraulically actuated dilator tip propagation mechanism in retracted form (FIG. 12A), in extended form (FIG. 12B), and including a three-lumen dilator shaft (FIG. 12C).

FIGS. 13 A-D illustrate cross-sectional views representing four consecutive configurational stages A-D for hydraulically propagating the "CTO Penetration Tip," as an embodiment.

FIGS. 14 A-D illustrate the inter-operability of the functional units for enabling in vivo "lesion-length selectivity" and deploying the FICS LLS PTA configuration in successive multi-level stages, as an embodiment.

DETAILED DESCRIPTION

A. Definitions

The term "a" refers to one or more modified nouns and/or pronouns.

The term "Functionally Integratable Catheter System" ("FICS System") refers to various combinations of the disclosed "functional units," wherein each unique combination is referenced herein as therapeutic-specific "configurations." The FICS System comprises at least five main "functional units," including: (a) FICS Support Catheter; (b) FICS Dilator; (c) FICS PTA Catheter; d) FICS Lock-Grip Handle; and (e) FICS Steering Hub. Each "functional unit" of the FICS System is further described in the following subsections, including figures, tables, and examples. FICS System enables continuous access to multiple number of lesions within an affected vessel by providing relative positional stabilization between the FICS Support Catheter and other "functional units" by maintaining the FICS Support Catheter in place, in contrast to conventional practices requiring the removal of generic support catheters and/or guidewires during therapeutic intervention. The cycle of dis-assembly and re-assembly may be repeated multiple times as necessary by clinical operators for treating an affected vessel in a continuous, multi-staged procedure.

The terms "configuration(s)" or "FICS configuration(s)" refer to therapeutic-specific combinations of the individual "functional units" that can be reversibly co-assembled, dis-assembled, and re-assembled by clinical operators (e.g., interventional physicians) to obtain multiple inter-operable devices (i.e., FICS System) suitable for treating any type of complex lesions/CTOs encountered during intervention. A visual map of the various "functional units" and "functional subunits" that can be selectively combined by a clinical operator for constructing specific "FICS configurations" most effective for treating a broad range of complex lesions and CTOs is referenced in FIG. 17.

Figure 17:
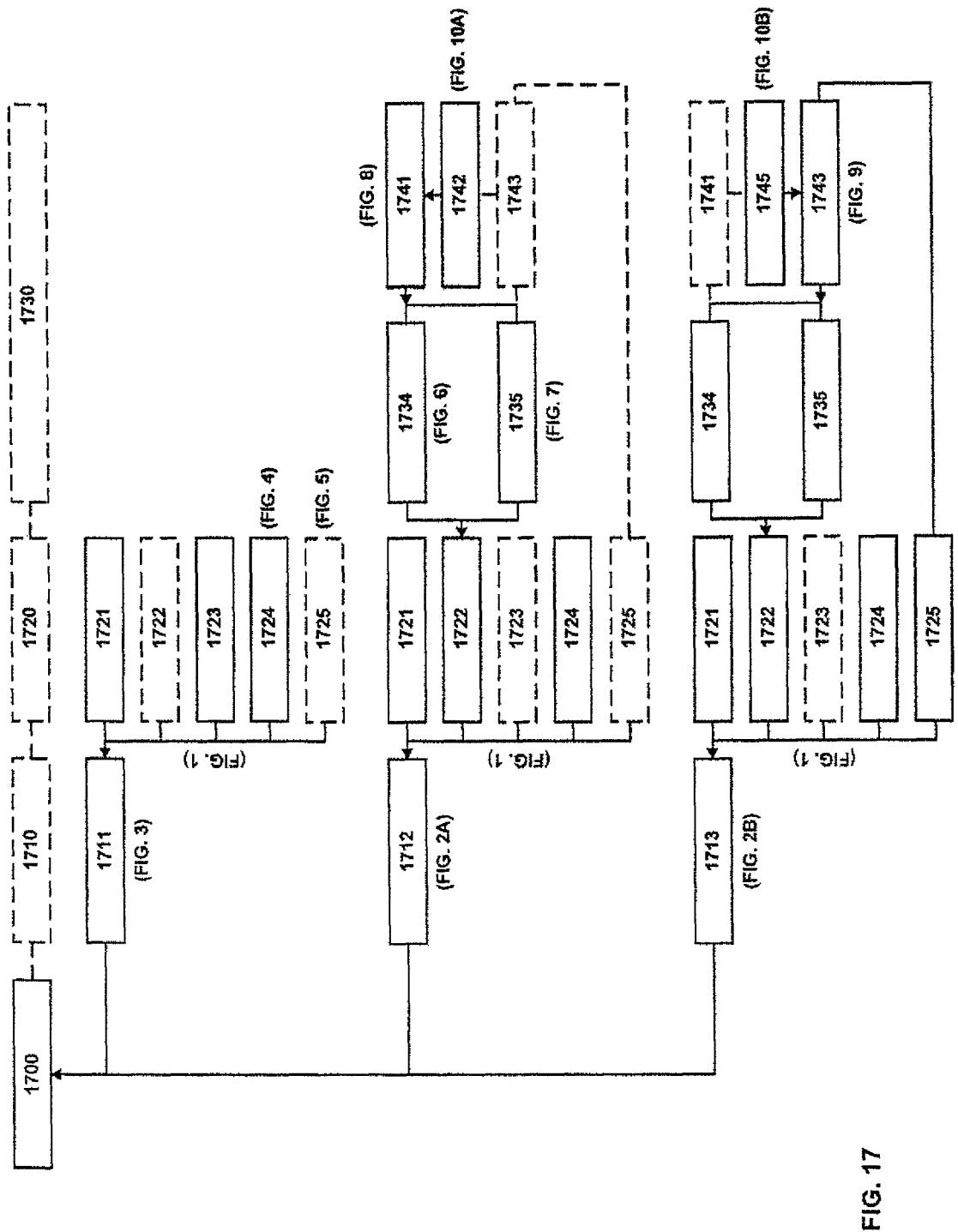
FIG. 17 is a flow-chart overview of the possible FICS System "configurations" as contemplated herein, providing a visual map of the various "functional units" and "functional subunits" that can be selectively combined by a clinical operator for constructing therapeutic-specific "configurations" most effective for treating a broad range of complex lesions and CTOs.

The term "functional subunits" refers to the "FICS subunits" that can be provided in pre-assembled states as optional configurational alternatives to enable/enhance a particular functionality of the highly adaptable FICS System by providing different therapeutic-specific "FICS configurations" as referenced in FIG. 17. In particular, several "design" options in constructing the various "CTO Penetration Tips" (FIGS. 6, 7, 8, and 9) and "Reentry Tips" (FIGS. 9 and 10) for the distal tip portion of the hydraulically actuated FICS Dilator are disclosed.

The term "pre-configured" refers to the state of a functional unit that is not assembled or configured together by a clinical operator to obtain one or more operable "FICS configurations" as referenced conveniently in FIG. 17.

The term "functionally integratable" refers to the capability of the "functional units" of the disclosed FICS System to be assembled together or interconnected into various therapeutic-specific "FICS configurations" having improved operational characteristics and benefits, as compared to the operational effectiveness of each pre-assembled functional unit. Each individual component may be operational in a pre-configured state, but having limited functionality as a standalone device, as compared to the enhanced performance characteristics expected of the dimensionally configured functional units (i.e., FICS configurations) represented in FIG. 17. As used herein, the functional combination (co-assembly/re-assembly) of the various "functional units" and "functional subunits" of the disclosed FICS System can be reversibly disassembled after use for a first medical procedure in preparation to be re-assembled into a different "FICS configuration" for use during a second subsequent medical procedure (e.g., for the treatment of a second lesion) in the same or different affected vessel.

The term "FICS Support Catheter" ("SC") refers to a stabilizing catheter positioned over a pre-disposed guidewire ("GW") that can protect delicate vessels during an interventional procedure by providing a structurally guiding shield for maneuvering other FICS "functional units" through the lumen space. As a specific feature, the SC comprises a distal working end (the section of an instrument that is useful for performing certain therapeutic procedures) that can be variably adapted by the physician by physically supporting and guiding the insertion of other FICS "functional units" as necessary for comprehensively treating complex lesions, including total occlusions.

The term "FICS Dilator" refers a "functional unit" useful for dilating affected vessels by initially creating an opening and subsequently forming an entryway for other FICS functional units such as the FICS LLS PTA Catheter and guide wires. The FICS Dilator comprises a shaft having a distal tip portion that can be projected distally by a hydraulically actuated mechanism. As a specific feature, the FICS Dilator has a distal working end that can be designed to incorporate specifically designed tips that can provide various functionalities for enabling intraluminal and/or extraluminal recanalization (FIGS. 6-10).

Figures 2A, 2B:
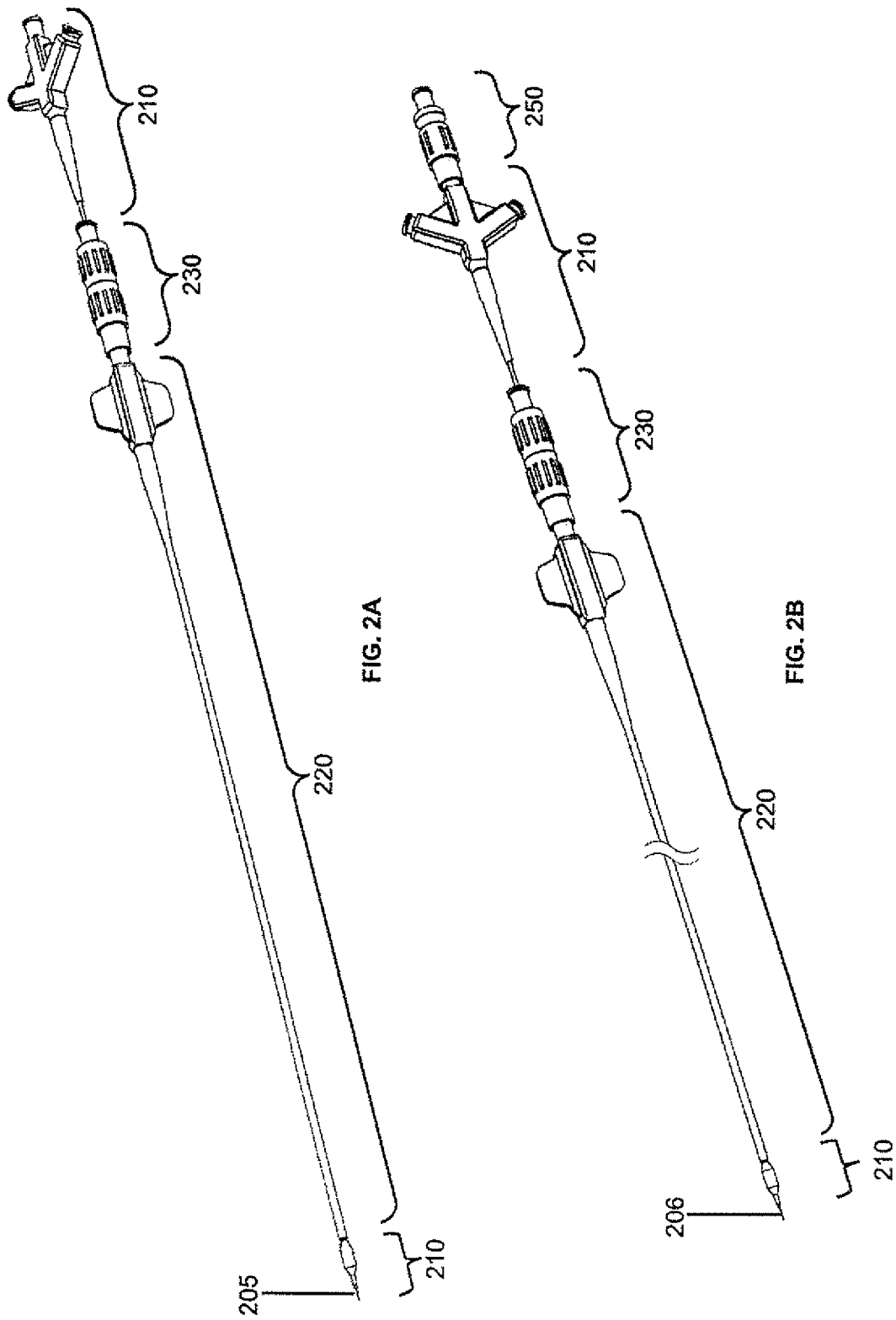
FIG. 2A shows an exemplary "CTO Penetration" design adaptable for a FICS CTO Dilator configuration suitable for intraluminal recanalization, as an embodiment.
FIG. 2B shows an exemplary "Reentry" design adaptable for a FICS Reentry Dilator configuration suitable for extraluminal recanalization, as an embodiment.

The term "FICS CTO Dilator" refers to a FICS configuration obtained by inserting the FICS Dilator incorporating a "CTO Penetration Tip" within the FICS Support Catheter intended for intraluminal recanalization (FIG. 2A).

The term "FICS Reentry Dilator" refers to a FICS configuration obtained by inserting the FICS Dilator incorporating a "Reentry Tip" within the FICS Support Catheter intended for extraluminal recanalization (FIG. 2B).

Figure 10B:
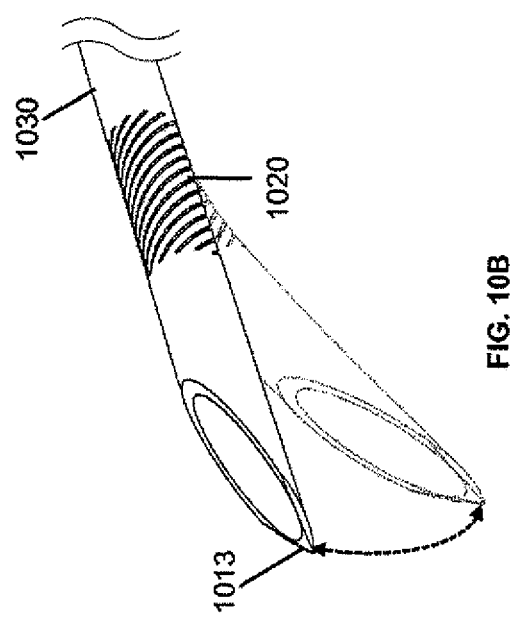
FIG. 10B is a magnified view of a "Reentry Tip" comprising a malleable and angled hypotube of a FICS Dilator, suitable for extraluminal recanalization, as an embodiment.
Figure 10A:
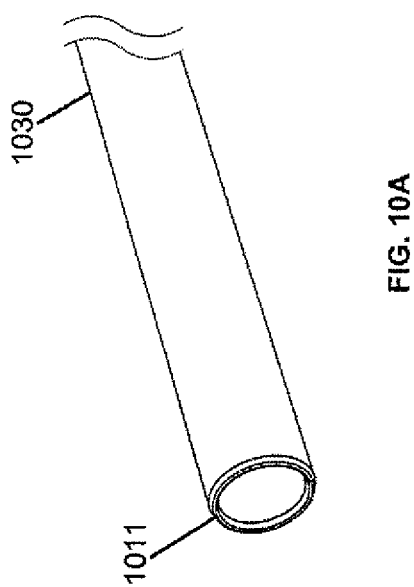
FIG. 10A is a magnified view of a "CTO Penetration Tip" comprising a non-malleable and blunt-ended hypotube of a FICS Dilator suitable for intraluminal recanalization, as an embodiment.

The term "CTO Penetration Tip" refers to various tip designs contemplated for constructing the dilator tip portions of the hydraulically actuated FICS Dilator that can be specifically adapted to be suitable for effecting CTO penetrations, applicable to the therapeutic-specific "FICS configurations" referenced in FIG. 17 (FIGS. 6-7, 10A).

The term "Reentry Tip" refers to various tip designs contemplated for constructing the dilator tip portions of the hydraulically actuated FICS Dilator that can be specifically adapted to be suitable for effecting subintimal access and reentry, applicable to the therapeutic-specific "FICS configurations" referenced in FIG. 17. The specialized tip design is intended for enabling extraluminal recanalization (FIG. 10B) that can be controllably managed by a Steering Hub (FIG. 5) as part of the "FICS Reentry configuration" (FIG. 2B). Furthermore, the FICS Reentry Tip can be controllably diverted by incorporating a flexible/shapeable tip segment (FIG. 10B). The "FICS Reentry Tip" can be most effective when combined with a torque-stable, steerable FICS Dilator (FIG. 9).

Figure 4:
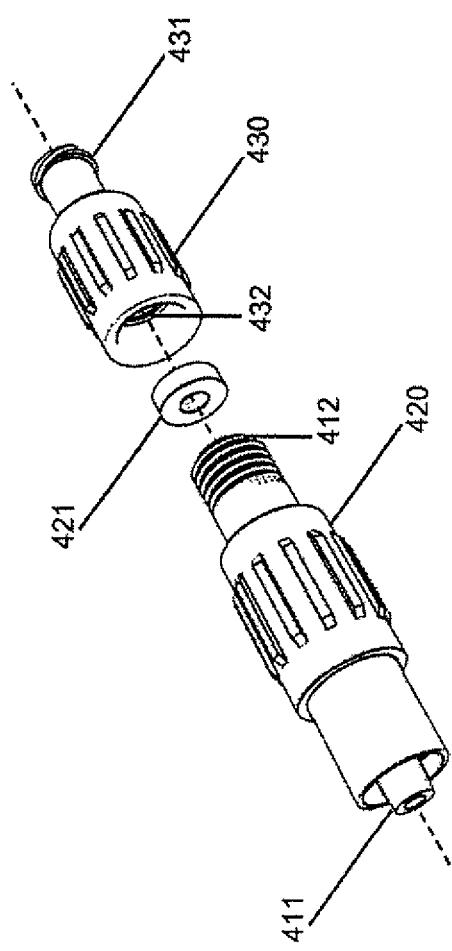
FIG. 4 is a perspective diagram illustrating the internal components of the FICS Lock-Grip Handle, as an embodiment.

The term "FICS Lock-Grip Handle" refers to an operational handle and a positional stabilization device for maintaining the co-assembled functional units in relative order, alignment, and position (FIG. 4).

The term "FICS Steering Hub" refers to an operational handle (FIG. 5) for controlling the directional steering of the co-assembled functional units in relative orientation, useful as part of the "FICS Reentry" configuration (FIG. 2B) involving "FICS Reentry Tips" (FIGS. 9 and 10B).

Figure 3:
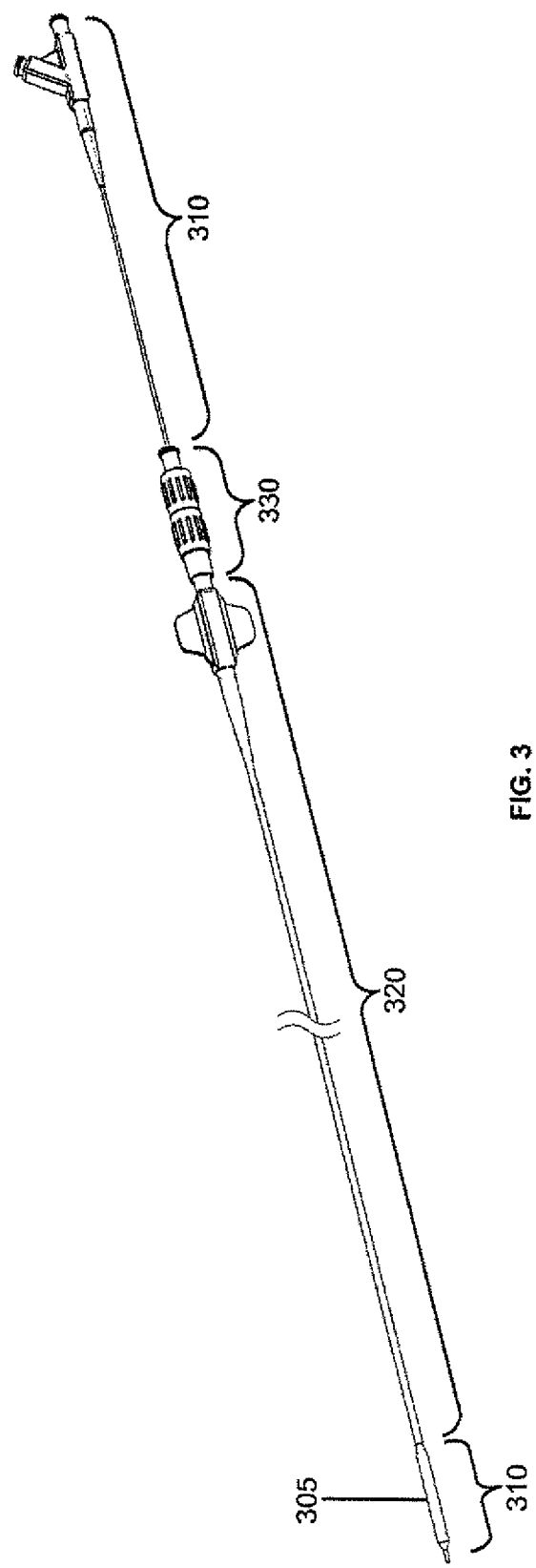
FIG. 3 illustrates the assembled "FICS LLS PTA Catheter" configuration useful for "lesion-length selectivity," as an embodiment.

The term "FICS PTA Catheter" refers to a catheter formed to include a PTA inflation member at the distal end (FIG. 1) that can be combined with other functional units to form the "FICS LLS PTA Catheter" (FIG. 3).

Figure 1:
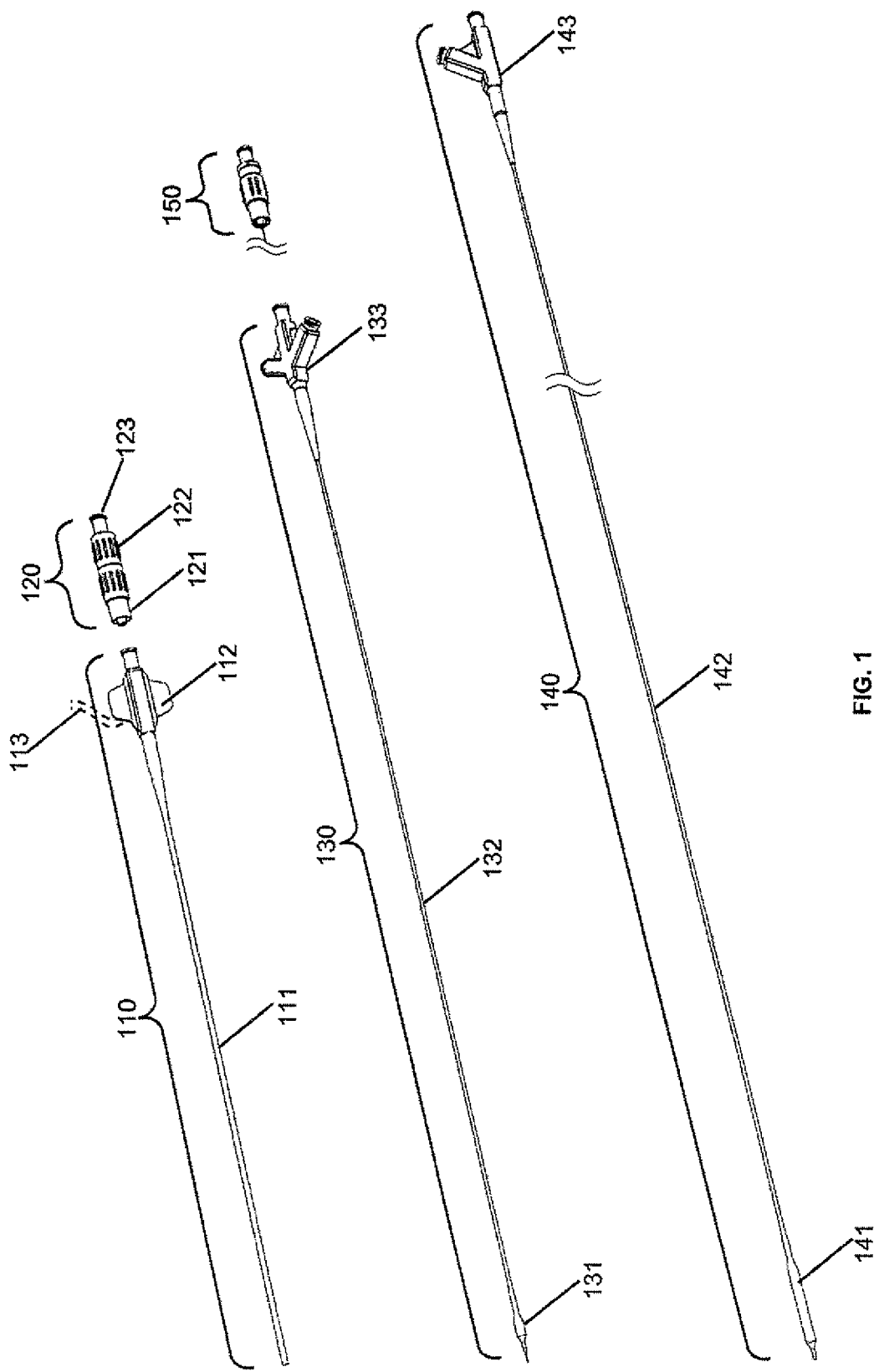
FIG. 1 illustrates the five main functional units of Functionally Integratable Catheter System (FICS) of the present disclosure in a pre-configured state, as an embodiment.
Figure 11:
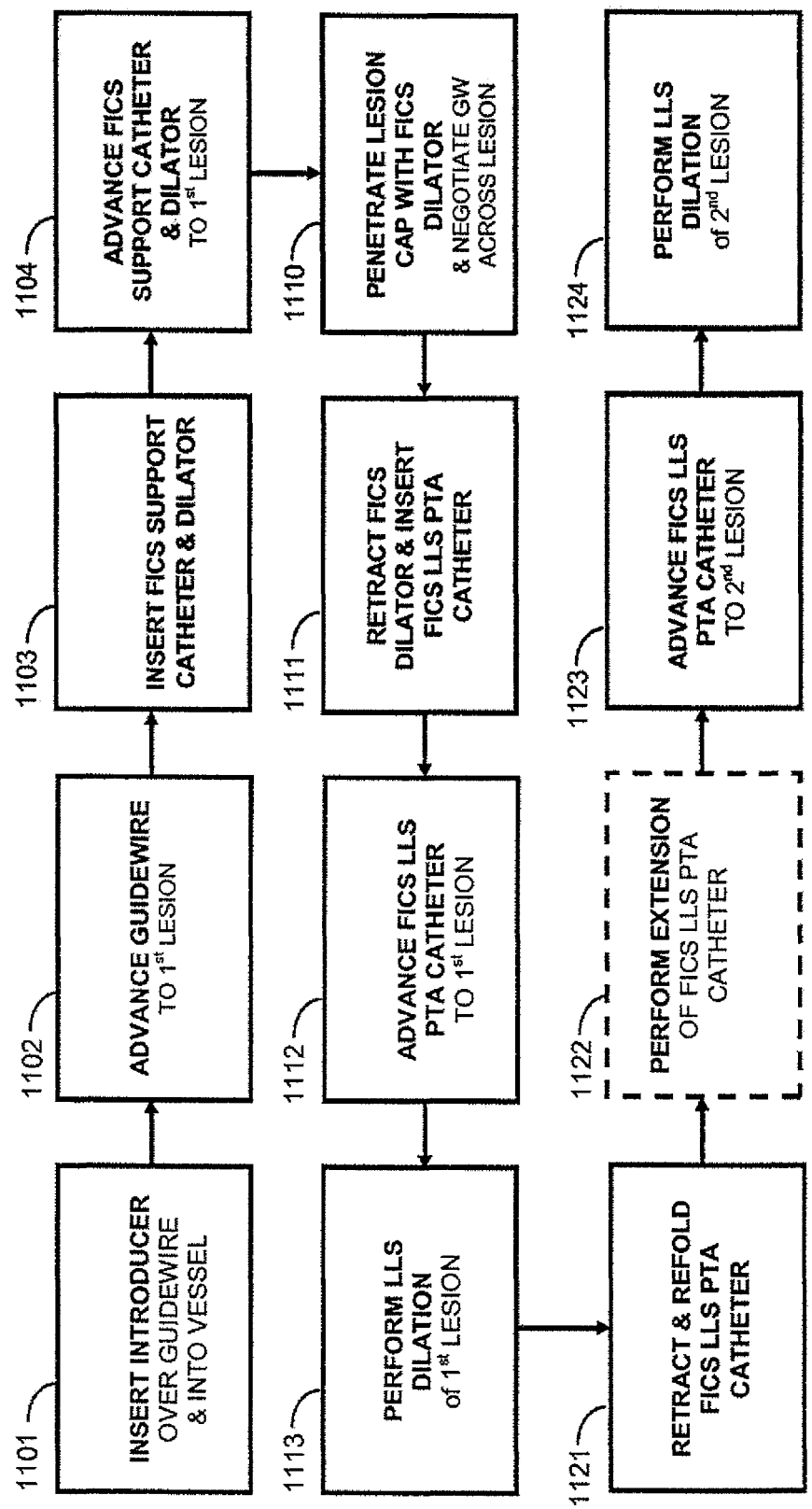
FIG. 11 is an exemplary flow diagram of a multi-staged angioplasty procedure performed in vivo for successive therapeutic treatment of complex lesions and CTOs utilizing the FICS System, as one embodiment.

The term "FICS LLS PTA Catheter" refers to the FICS configuration (FIGS. 3 and 14) resulting from functionally combining: (a) FICS Support Catheter (FIG. 1); (b) FICS PTA Catheter (FIG. 1); and (c) FICS Lock-Grip Handle (FIGS. 1 and 4). The balloon-length and balloon-diameter adjustability features of the FICS LLS PTA Catheter confer the "lesion-length selective" functionality (FIG. 16) for performing multi-level angioplasty procedures (FIG. 11).

The term "intraluminal recanalization" refers, in referencing the FICS System in this disclosure, to the restoration of perfusion through affected vessels by an interventional procedure mediated within the lumen of affected vessels, wherein the distal tip of the hydraulically actuated Dilator is intended to function within the lumen of the treated vessels.

The terms "extraluminal recanalization" refers, in referencing the FICS System in this disclosure, to the restoration of perfusion through affected vessels by an interventional procedure mediated through the subintimal layers of affected vessels, wherein the distal tip of the hydraulically actuated Dilator is intended to pass through the subintimal layers of the treated vessels before reentering the lumen at a site distal to a CTO or complex lesion. In effect, the "extraluminal recanalization" enables the creation of an alternative blood flow passage by forcibly separating the subintimal layers surrounding the CTO/complex lesion and forming an alternative conduit to restore perfusion.

The term "Total Length" (TL) refers to the total length of the FICS System or individual functional units.

The term "Usable Length" (UL) refers to the indwelling/working length portion of the FICS System or the individual functional units.

The term "Sheath Compatibility" refers to the maximum instrument outer diameter (OD) along the UL that can be introduced through an introducer sheath of commensurate inner diameter without resistance.

The term "guide wire compatibility" refers to the minimum inner diameter (ID) of the lumen of a functional unit/instrument for passing a guidewire of certain outer diameter without resistance.

B. Procedural Risks and Limitations of Current Medical Devices and Procedures for Treating Total Chronic Occlusions (CTO) and Complex Atherosclerotic Occlusions/Lesions Atherosclerosis can be generally classified into coronary, neurovascular or peripheral vascular disease subtypes, involving the progressive deterioration of cerebral, carotid, coronary, renal, hepatic, aortoilliac, iliac, gonadal, femoral, popliteal, and below-the-knee (BTK) arteries and veins. The diseased body can compensate for the gradual impairment of vascular functions by forming alternative collateral vessels in order to maintain adequate blood supply to dependent tissues and organs. However, such compensation mechanisms are only temporarily effective, and are marginally adequate for sustainably perfusing dependent tissues/organs. Insufficient perfusion of critical organs can have devastating effects, often resulting in one or more increasingly severe complications that can be triggered/exacerbated by atherosclerotic vessels, including: angina pectoris, myocardial infarction (MI) and congenital heart failure, often leading to patient mortality. Patients suffering from a peripheral vascular disease, resulting from the blockage of one or more peripheral blood vessels, are highly likely to experience the onset of multiple related complications (in the order of disease severity): claudication, ischemic rest pain, ulcerations, critical limb ischemia (CLI), gangrene, and/or tissue necrosis. In addition to raising the risks for requiring surgical interventional procedures, including bypass placement and limb amputations, some acutely life-threatening complications caused by vascular diseases may increase the risks for developing embolisms and strokes.

Lack of adequate perfusion through narrowed, stenotic, or occluded blood vessels can be treatable by various interventional procedures that can be suitably selected for patient-specific situations, taking into consideration several clinically relevant factors. In general, effective therapeutic interventions may involve systemic administration of one or more suitable pharmaceutical agent(s) in conjunction with minimally invasive, locally administered interventional procedures requiring the application of one or more atherectomy devices, balloon dilation catheters, and/or stents by a practicing clinician. For example, a balloon dilation catheter can be utilized for treating (a) coronary vessels during a "percutaneous transluminal coronary angioplasty" (PTCA); and (b) peripheral vessels can be utilized during a "percutaneous transluminal angioplasty" (PTA). However, if lesions, malformations, constrictions, obstructions and blockages within arteries/veins are not effectively treatable by standard vascular interventional therapy, then surgical intervention may be necessary, including "open surgery" effective for surgically forming a bypass composed of an autograft vein removed from a patient, or by forming a synthetic graft around the diseased vessel segment. However, if tissue damage is deemed irreversible beyond salvage, then bypass or surgical amputation of the affected limb may be the only option. Generally, surgical treatments can pose substantial risk and trauma for many symptomatic patients. Even if the outcome is deemed successful, the surgery may leave a profound and permanently debilitating impact on patients' mobility, life expectancy and overall quality of life.

As an effective and less risky alternative to drastic surgical procedures, interventional procedures have become more widely accepted and modestly practiced, if warranted by patient-specific circumstances. To propose treatment strategies and recommendations for the management of peripheral arterial disease, the European Society of Vascular Surgery and the World Federation of Vascular Surgery Societies have published the Trans-Atlantic Inter-Society Consensus document (TASC; 2000, TASC II; 2007). These recommendations provide general guidance for treating various types of lesions depending on their dimensions (length, diameter), degree of occlusion, and type of affected vessels. According to the "Consensus document," the "TASC A" lesions (least severe) have been deemed most suitable for endovascular procedures, and surgery has been primarily recommended for most severe cases, such as "TASC D" lesions. These "Type D" lesions can refer to either "chronic total occlusion" of the common or superficial femoral artery (>20 cm) involving the popliteal artery), and "chronic total occlusion" of the popliteal artery and proximal trifurcation vessels. However, endovascular therapy for complex lesions of the superficial femoral and popliteal artery remains controversial. This TASC document acknowledges that more clinical evidence may be required to base firm recommendations for treating TASC B and C lesions by PTA procedures. "Type B" lesions can be assigned for conditions involving multiple lesions (55 cm) (e.g., stenoses or occlusions); single stenosis or occlusion (515 cm) not involving the infrageniculate popliteal artery; single or multiple lesions in the absence of continuous tibial vessels to improve inflow for a distal bypass; heavily calcified occlusion (55 cm); and single popliteal stenosis. "Type C" lesions can be assigned for conditions involving multiple stenoses or occlusions (>15 cm) with or without heavy calcification, and recurrent stenoses or occlusions that have been previously treated by two endovascular interventions.

In particular, chronic occlusions represent a significant portion of vascular pathologies, and have historically presented a serious technical challenge for interventional practitioners that rely on conventional guide wires and catheters for accessing plaques/lesions. The treatment outcomes depend on the morphological and compositional characteristics of a given chronic total occlusion, in that softer and less compacted CTO plugs can be relatively easier to displace as compared to densely calcified CTO caps that may be impenetrable in the most challenging situations. Thus, "chronic total occlusions," which may be considered as a separate clinical pathology most commonly encountered in TASC D lesions, can remain procedurally challenging when treated by percutaneous transluminal angioplasty, contributing significantly to procedural failure rates for peripheral interventions. Despite the various technical challenges associated with CTO treatments, such minimally invasive interventional vascular approaches have been increasingly preferred as the first option for treating peripheral disease conditions to avoid substantial risk of mortality associated with conventional bypass surgery. Unfortunately, the success rates for intraluminal and subintimal CTO recanalization techniques as conventionally practiced using conventional guide wires and catheter devices remain only moderate at best. There is a persistent need to provide various patient-adaptable interventional devices that can be customized by physicians for more effective treatment of vascular conditions/diseases, such as associated complex lesions and CTOs.

As a first procedural step, percutaneous guidewire negotiation by intraluminal intervention can be attempted to cross and recanalize chronic occlusions. However, the application of standard guide wires and catheter devices to enable percutaneous intraluminal recanalization of CTOs have shown only moderate procedural success. Failure in guide wire negotiations can lead to failure in CTO recanalization. Factors that may significantly impact the prospective outcome include: lesion length, patient-specific anatomical tortuosity, lesion-cap calcification, medical operator skill and presence of run-off vessels. In more recent years, subintimal recanalization with distal reentry, known as percutaneous intentional extraluminal recanalization ("PIER"), has been increasingly advocated as a viable alternative approach when intraluminal passage remains procedurally unsuccessful. This technique has been applied with considerable technical success for superficial femoral artery (SFA) angioplasty, where multi-segmental, extended, calcified occlusions exhibiting mean occlusion lengths of 15 cm can be regularly observed.

Subintimal CTO recanalization approaches have been somewhat successful, although the technique itself may not be applicable in all cases. Typically, subintimal CTO recanalizations require most advanced levels of physician experience, skills, and general expertise because controlling the reentry into the true lumen of a target vessel and finding positional control of the reentry site can be potentially problematic for the inexperienced and/or unskilled. For example, vessel trauma and uncertain complications may result if reentry site is extended significantly and distally from the targeted vessel lumen region, thereby increasing the likelihood for subsequent subintimal angioplasty or stenting to be required inadvertently beyond the occluded vessel section. In the worst case scenario, improper guide wire negotiation for CTO recanalization can cause vessel trauma, rupture, dissection and/or bleeding due to inadvertent vessel wall perforation. A certain level of flexibility is desirable for guide wire tip sections and distal shaft portions, which enables efficient, atraumatic vessel navigation. When attempting CTO penetrations, however, this flexibility can cause the guide wire tip and shaft sections to buckle or kink, and can negatively impact the overall positional controllability of the guide wire, affecting device stability during implementation. The guide wire tip may be deflected from the typically hardened cap surface region of the CTO, causing the tip to veer eccentrically away from densely calcified plaque tissue into adjacent soft vessel walls. Once a subintimal passage has been inadvertently formed, the subsequent application of adjunct therapeutic devices, such as atherectomy catheters or balloon dilation catheters, can be substantially impeded or procedurally prohibited. Furthermore, the guide-wire penetration capability can be directly proportional to the shaft stiffness, which can be inversely proportional to having navigational flexibility, and therefore, the relatively flexible guide wire may require some additional form of guiding support to provide a safe yet effective measure of pushability.

As is the case for most medical devices, the various interventional devices and procedures for treating vessel occlusions have not satisfied all procedural challenges encountered during practical applications. Most interventional physicians must rely on device manufactures to provide all necessary equipment and implements in treating a broad spectrum of lesions/occlusions exhibiting different lengths, density, and severity. This limitation becomes acute especially for the treatment of complex lesions and total occlusions, where it is common for physicians to improvise in "arranging" their own "custom" devices by recombining various approved medical device components to devise a "make-shift" or workable combinations for those situations where a single pre-made device can be insufficient and alternatives are non-existent. Many medical devices and implements can serve multiple general functions and may not be designed for a specialized end use and/or devices made by different manufactures may not be functionally compatible to work together due to different material properties and/or dimensional configurations. Under the current circumstances, significant expertise and skill can be required to recanalize multiple numbers of chronic total occlusions in a single or multiple vessels. Significant physician judgement can guide procedural decisions as to the optimal combination of different medical device components to affect a desired therapeutic outcome. Technical challenges can include the selection and dimensional matching of various medical device components that can work well together during multi-staged, complex procedures. Seasoned expertise can be required for orchestrating the procedural combination of such medical device components that can be optimally positioned for highly variable, patient-specific clinical situations. An improved system would enable physicians of any skill level to effectively treat the most challenging and complex occlusions more conveniently in less time at significantly reduced cost.

C. Functionally Integratable Catheter System"
("FICS") for Treating Complex Atherosclerotic
Lesions/Occlusions The present disclosure provides a comprehensive multi-functional device platform that can be variably configured by clinician operators for patient-specific anatomies and clinical situations for treating complex and total occlusions. This device platform enables physicians of any skill level to effectively treat the most challenging and complex lesions/occlusions more conveniently in less time. The present disclosure provides a Functionally Integratable Catheter System ("FICS System") representing a system of "functional units" that can be configured together to operate synergistically. FICS System comprises at least five main "functional units," including: (a) FICS Support Catheter; (b) FICS Dilator; (c) FICS PTA Catheter; (d) FICS Lock-Grip Handle; and (e) FICS Steering Hub. Each "functional unit" can be provided in a pre-assembled form by the manufacturer, and optionally co-packaged as a device tray that includes the functional units (a)-(e), intended to be configured into variable combinations ("FICS configurations") by clinician operators. In particular, examples of therapeutic-specific "functional subunits" include the various "CTO Penetration Tips" and "Reentry Tips" disclosed herein, wherein each tip design can be designed specifically for treating a particular type of complex lesion and/or CTO. Any FICS configuration that includes the FICS Dilator incorporating a "CTO Penetration Tip" can be utilized for facilitating intraluminal recanalization. Any FICS configuration that includes the FICS Dilator incorporating a "Reentry Tip" can be utilized for facilitating extraluminal recanalization. Although each of the individual "functional units" may be operational in a pre-configured state, each functional unit may have limited functionality as a standalone device, as compared to the synergistic effect that can be achieved by utilizing the FICS System representing a comprehensive multi-functional device platform that can be highly adapted for treating any complex lesions and CTOs affecting both vascular and non-vascular tissues by providing several therapeutic-specific configurations as referenced in FIG. 17.

Many patients suffering from advanced atherosclerosis demonstrate multiple complex lesions along a common affected vessel, meaning that therapeutic intervention requires the sequential treatment (access, recanalization, and dilation) of all plaques/lesions in order to restore patency to sufficient levels. FICS provides a set of inter-operable functional units (a)-(e) conceptually analogous to a broad range of situation-specific implements that can be co-assembled by physicians. After employing a first hypothetical FICS configuration in a first interventional procedure (i.e., treatment of the first occlusion), the FICS functional units can be reversibly disassembled in order for the functional units to be reassembled into a different configuration for a second subsequent interventional procedure (i.e., treatment of the second occlusion), in the same patient if necessary. The cycle of dis-assembly and re-assembly may be repeated multiple times as necessary by clinical operators performing simultaneous and/or sequential applications in viva. The interoperability of FICS functional units with a pre-deployed guidewire means that: (a) the FICS SC and GW can remain in situ without having to retract either of these for repositioning in order to treat a second or subsequent lesion present in the affected vessel undergoing treatment; (b) access to multiple number of lesions can be continuously maintained; (c) procedural steps can be reduced saving time/cost; (d) quality of the procedure can be increased; and (e) operational convenience can be significantly improved.

Various embodiments are directed to the FICS components that can be assembled into various "functional units." Various embodiments are directed to the specific configurations that can be assembled together by combining different FICS "functional units" in order to be particularly customized for different types of vascular conditions in need of treatment. Various embodiments are directed to methods for manufacturing the FICS "functional units." Various embodiments are directed to the methods for treating vascular and/or non-vascular diseases utilizing one or more FICS configurations as a therapeutic implement for facilitating several functionalities, including more effective: (a) guide-wire negotiations; (b) lesion penetrations; (c) recanalizations; (d) vessel dilations; and (e) vessel-lumen restorations.

D. Co-Assembling the Functional Units of the Functionally Integratable Catheter System ("FICS")

The Functionally Integratable Catheter System ("FICS System") includes at least five main "functional units": (a) FICS Support Catheter; (b) FICS Dilator; (c) FICS PTA Catheter; (d) FICS Lock-Grip Handle; and (e) FICS Steering Hub. These "functional units" can be designed to operate synergistically, and can be configured together by clinician operators before/during multi-staged procedures for treating complex lesions/total occlusions. In one preferred embodiment, all functional units can be packaged together as a device tray that includes functional units (a)-(e), intended for co-assembly into variable configurations by clinical operators (a physician and/or operating professionals). In another preferred embodiment, each type of functional unit (a) (e) can be packaged separately to be provided as a replacement component. All functional units can be configured and dimensioned for complete interoperability/compatibility.

In the following subsections, each of the referenced functional units (a)-(e) are described in further detail to specify respective structural and functional characteristics in FIGS. 1-17. Dimensional characteristics are described in the Examples and Tables 1-7. For convenience, FIG. 17 provides a flow-chart overview of the possible FICS System "configurations" as contemplated herein, providing a visual map of the various "functional units" and "functional sub-units" that can be selectively combined by a clinical operator for constructing therapeutic-specific "configurations" most effective for treating a broad range of complex lesions and CTOs.

1. Operational Configurations for FICS System 1.1 the Pre-Configured Functional Units of FICS System FIG. 1 shows the five main functional units of Functionally Integratable Catheter System (FICS) of the present disclosure in a pre-configured state. In FIG. 1, the Functionally Integratable Catheter System (FICS) is represented as five separable components (from top to bottom): (a) Support Catheter 110; (b) Lock-Grip Handle 120; (c) Dilator 130; (d) PTA Catheter 140; and (e) Steering Hub 150, wherein these separable "functional units" can be co-assembled and re-assembled together by clinical operators in various combinations suitable for particular therapeutic purposes ("therapeutic-specific configurations"). The Support Catheter, the Dilator, and the PTA Catheter are each dimensionally adaptable for interoperability. The variable total length (TL) of the configured system is dimensionally adaptable within a range of approximately 90-220 cm, and wherein the variable usable length UL is dimensionally adaptable within a range of approximately 60-180 cm, as further described in the Examples and Tables 1-7.

In FIG. 1, the FICS Support Catheter 110 comprises a shaft member 111, one or more flushing ports 113, and a manifold member 112 with a female luer lock adapter, which can be connected to the FICS Lock-Grip Handle 120 comprising a male luer adapter 121, an external casing member 122, a hemostatic valve portion formed within 122, and a female luer adapter 123. The support catheter further comprises a central lumen that receives the insertion of the dilator or the PTA catheter for enhancing manuverability, and wherein the distal edge of the pre-configured Support Catheter is straight-edged for an interoperable design, unlike conventional Support Catheters having a tapered distal edge. The straight edge of the Support Catheter is a design feature that improves the interoperability between the Support Catheter and the dilator/PTA catheter when operationally joined; and is functionally augmented by insertion of other functional units to form a seamless, atraumatic edge upon their combination (FIG. 14A). The straight distal edge may include a reinforced tip region, wherein the reinforcement comprises a radiopaque material. As related embodiment, the FICS Support Catheter shaft and tip region can be formed from a flexible polymer, wherein the polymer may contain braided mesh embedded as structural reinforcement. The reinforced tubing and reinforced tip region can be designed to withstand positive and negative pressures exerted on the system, including both nominal balloon inflation pressure ranges and ranges exceeding burst pressure. At substantially the same time, the reinforcement can physically constrain the radial expansion of an inflatable member portion sheathed/coaxially received therein. Furthermore, such semi-rigid material compositions/combinations can provide for improved (a) device pushability; (b) directional bending capability; and (c) mechanical support for enhancing vessel guidance. As another embodiment, the FICS Support Catheter includes one or more flushing orifices that can be incorporated on the proximal lateral surface of the distal edge for providing and aspirating contrast fluid and saline solutions utilized during interventional procedures, wherein these orifices can be maintained fluidly connected to the central lumen of the Support Catheter; and wherein the fluids can be transferred via one or more flushing ports (113) integrated into the SC manifold in the presence or absence of other insertable functional units. The flushing port can be integrated into the manifold as a separate luer inlet, or alternatively, the manifold may be configured to contain a two-way valve attached to the flushing port to enable media transport and to enable aspiration, perfusion and suction functionalities. The manifold may further comprise an additional balloon introducer and/or a hemostatic seal with an optional locking mechanism operationally coupled to the manifold to temporarily fixate/stabilize together multiple FICS functional units. As another embodiment, the FICS Support Catheter can include one or more distally positioned radiopaque markers placed along the shaft surface (e.g., proximal to the distal tip) to enable angiographic device visibility, such as for tracking the tip position within treatable vessels. As another embodiment, the FICS Support Catheter includes one or more visual or haptic surface markings for aiding the co-assembly of the FICS functional units as a positional guidance for user convenience (e.g., indicating the location of flushing holes). As another embodiment, the support catheter can be used as an introducer sheath within specific clinical use scenarios, for example, when performing an interventional procedure via radial or brachial access, thereby effectively reducing the number of components required. As related embodiment, the FICS Support Catheter can function as an aspiration catheter in the absence or presence of other FICS functional units.

In FIG. 1, the FICS Lock-Grip Handle 120 can function as a user handle for physician operators. As a critical operating element for FICS products, the Lock-Grip Handle 120 can provide relative positional stabilization (fixation, length adjustment and hemostatic sealing) for the interconnecting functional units, improving the general handling of the system. The FICS Lock-Grip Handle can be designed as a simple polymeric cylinder, clip, wedge or screw that can be reversibly attached to the FICS Support Catheter or any of the following: FICS Dilator, FICS PTA Catheter, FICS Steering Hub. As another embodiment, the FICS Lock-Grip Handle can be attached at the proximal, non-indwelling shaft portion of the FICS Support Catheter. Operational coupling of the FICS Lock-Grip Handle to the other FICS functional units can provide relative positional stabilization, including longitudinal distance adjustment between the units. The internal hemostatic seal of the FICS Lock-Grip can be designed to accommodate coaxially receivable functional units of varying diameter. The FICS Lock-Grip Handle can include visual, acoustic or haptic markings for improved length adjustability and handling by clinical operators. As another embodiment, the FICS Lock-Grip Handle can be configured to simultaneously attach to the FICS Support Catheter and FICS Dilator in order to expose the balloon length formed between the FICS Support Catheter as the outer sheath and the inflatable member of the FICS Dilator. As another embodiment, the FICS Lock-Grip Handle can be provided firmly attached to the FICS Support Catheter, by methods known to persons skilled in the arts such as thermal or adhesive bonding, welding, gluing, screwing, snapping, clipping, interference fit, insertion and/or coaxial alignment. As another embodiment, the FICS Lock-Grip Handle can be mechanically coupled to coaxially receive the FICS Dilator by mechanically adhering, snapping, sliding, screwing, clipping, wedging or keying into the dilator shaft. As another embodiment, the FICS Lock-Grip Handle can include a hub, an adaptor, a connector, a fitting, a jack or a socket configured to receive an interlocking or mating surface element of coaxially receivable components. As another embodiment, the FICS Lock-Grip Handle provides a mechanical end stop, limiting the longitudinal displacement of either the FICS Dilator shaft, the tip, and/or the FICS PTA proximal balloon cone. The FICS Lock-Grip Handle is further described in FIG. 4.

In FIG. 1, the FICS Dilator 130 comprises a dilator tip 131, a shaft member 132 and a manifold member 133. The FICS Dilator can incorporate optional structural features to provide multiple functionalities. As related embodiments, the FICS Dilator may include: (a) a distally positioned, non-anchoring (non-inflatable) dilator tip segment having dual lumen configuration, wherein a first lumen is a GW lumen and a second lumen is an actuation lumen that can be fluidly connected to an annular hydraulic chamber coaxially formed around a portion of the guide wire lumen; or (b) a distally positioned, anchoring and centering (inflatable) dilator tip segment with triple lumen configuration, wherein a first lumen is a GW lumen, and a second lumen is a tip actuation lumen fluidly connected to an annular hydraulic chamber coaxially formed around a portion of the GW lumen, and a third lumen is an inflation lumen for the inflatable member; wherein the hydraulic chamber is formed between the proximal lateral surface of a distal seal/gasket, the distal lateral surface of a proximal seal/gasket, the internal surface of an elongated outer tubular member forming the dilator shaft, and the external surface of an inner tubular member coaxially received therein. The distal seal/gasket extends from the external surface of the inner tubular member, wherein the proximal seal/gasket extends from the inner surface of the elongated outer tubular member. The inner tubular member can be formed as a hollow bore hypotube, further comprising a tip (lancet), and coaxially embedded into the aforementioned distal dilator tip segment, having one or more circumferentially positioned gaskets sealingly engaged with a portion of the annular hydraulic chamber and fluidly connected to the tip actuation lumen, wherein the hypotube tip (lancet) can be configured as a directionally non-steerable or steerable, hydraulically actuatable component, reversibly extensible along a length portion of the distal dilator tip, and can be sheathed/concealed therein during transport, wherein the one or more gaskets serve as mechanic end stops limiting the (longitudinal) extension range of the hypotube tip (lancet). As another embodiment, the FICS Dilator can contain a substantially rigid tip region or segment (capable of occlusion penetration), which can be embedded or partially encapsulated within a tapered, substantially soft polymeric material, to facilitate atraumatic vessel guidance and effective occlusion penetration capability. As another embodiment, the rigid tip can be manufactured from a tubular member, such as a hypotube. In another embodiment, the tip and selected shaft regions of the FICS Dilator comprise elements and/or structures of dissimilar mechanical properties to facilitate variable stiffness portions along defined length sections of the dilator shaft. As another embodiment, the tapered dilation tip can form a seamless and atraumatic transition to the support catheter shaft or mantle. The distal shaft section of the FICS Dilator can have affixed one or more inflatable members that can function to controllably center and safely anchor the dilator in the target vessel region. As another embodiment, one or more distally positioned, radiopaque markers can be placed on the dilator shaft surface to enable angiographic device visibility for precise positional verification. The hypotube tip shape and construction may be modified to be suitable for forming an inflexible/rigid "CTO Penetration Tip" or a flexible/malleable "Reentry Tip." FICS Dilator is further described in FIGS. 2 A-B, 5-9, 10 A-B, 15, and 17. The FICS Dilator shaft can be designed to comprise of a substantially incompressible shaft material, such as a metal or a rigid polymer, and can be provided reinforced.

In FIG. 1, the FICS PTA Catheter 140 comprises an inflatable member (a balloon) 141, a catheter shaft 142, and a manifold member 143. The FICS PTA Catheter can incorporate standard features found in other PTA catheter products. However, in contrast to other PTA catheters, the FICS PTA Catheter includes an inflatable member portion of constant length that can be concentrically concealed within an outer sheath formed by the FICS Support Catheter. During operation, the balloon member of the PTA can be advanced from the distal portion of the Support Catheter, controllably exposing an inflatable portion of the balloon member to a desired length capable of effectively dilating the length of a target lesion situated along an affected vessel in need of treatment. The length of the inflated portion of the balloon can be adjusted to the length of the target lesion so that by providing a prolonged balloon of a fixed length (having an adjustable operational length ranging approximately from 0 to 30 cm), lesions of various lengths can be dilated/treated by adjusting the length of a single balloon that can be controllably inflated at desired lengths to match the respective lengths of target lesions typically encountered during intervention. For example, a shorter inflated portion of the balloon would be suitable for dilating the full length of a shorter target lesion of comparable length. Similarly, a longer inflated portion of the balloon would be suitable for dilating the full length of a longer lesion of comparable length. Furthermore, multiple radiopaque markings can be provided both a) at the distal end of the support catheter shaft; and (b) at the distal end of the balloon, to provide visual guidance for determining the length for the balloon exposed from the support catheter and in the inflated state. The variable usable length of the PTA Catheter correlates with the variable usable length of the inflatable member (balloon) by enabling a clinical operator to control the length of the balloon that can be exposed from the Support Catheter during the in vivo "lesion length selective" balloon dilatation process. First, the FICS PTA Dilation Catheter can be inserted into the FICS Support Catheter and stabilized utilizing the Lock-Grip Handle to form an in situ "length selective" FICS LLS PTA configuration capable of treating lesions of variable lengths utilizing a single prolonged balloon member that can be inflated at variable lengths. The FICS PTA catheter and the inflatable member portion can be reversibly removed from the FICS Support Catheter during operation. The length of the Support Catheter can be dimensionally configured so that a minimum balloon length (the recessed portion shown as functional dimension "C" of FIG. 15, and Table 2) can be restricted from inflating by maintaining permanently receded (sheathed) within the distal end of the Support Catheter during the inflation and deflation processes, to retain the original balloon folding capability for enabling multistage PTA treatments and to preserve the optimal shape of the inflatable portion of the balloon. The FICS PTA catheter shaft can be composed of a substantially incompressible material, for example a hypotube formed from metal or rigid polymeric or a reinforced shaft.

In FIG. 1, the FICS Steering Hub 150 can function as a steering handle for physician operators. As a critical operating element for the FICS Dilator, the Steering Hub 150 can provide steering capability for directing the movement of the hydraulically actuated dilator tips ("CTO Penetration Tips"; "Reentry Tips"), improving the general handling of the system. The Steering Hub is further illustrated in FIG. 2B and is further described in FIG. 5. The Steering Hub can be particularly utilized for controlling the directional orientation for various dilator tips as shown in FIGS. 6-7, and FIG. 9, utilizing a Reentry Tip as illustrated in FIG. 10. The FICS Steering Hub can incorporate optional structural features for providing multiple functionalities. As related embodiments, the FICS Steering Hub can include visual, acoustic or haptic markings for improved directional orientation/adjustability and handling by clinical operators. As another embodiment, the rotational orientation modes facilitated by the Steering Hub assembly can be implemented in step-wise radial increments or in freely rotatable operation. The orientation of rotation as managed by the Steering Hub may be temporarily locked in individual, marked positions, or may be facilitated through a frictional resistance threshold (e.g. torque) of the operating members.

1.2 FICS Operational Configurations/Assembly of Functional Units

These separable "functional units" of the Functionally Integratable Catheter System (FICS) can be sequentially assembled/reassembled into different functional configurations, by physician operators, intended to be selectively adjustable for each phase of a multi-staged angioplasty procedure. The FICS configurations can be variably customized by a practicing physician to be suitable for different challenging situations encountered in treating patients who are seriously affected with advanced stages of arteriosclerosis (i.e., multiple lesions, extended lesion lengths, tortuous anatomy, total occlusions). For clinical situations involving chronic total occlusions, target obstructions must be either intraluminally penetrated (by passing through the CTO cap directly) or extraluminally circumnavigated (by passing through the subintimal vessel wall), before crossing and dilating the affected lesion/occlusion regardless of the variability in lesion length, lesion texture, and vessel anatomy. The presence of multiple lesions requires sequential treatment for each lesion/occlusion having certain length/texture characteristics. An ideal therapeutic instrument would be amenable to in vivo adjustment by a user for therapeutic-specific applications. The multi-configurational operation of the FICS functional units can provide a number of advantages: (a) procedural/clinical effectiveness in treating multiple and most severe complex lesions/CTO's; (b) substantial operational freedom/flexibility due to interoperable functional units enabled for reversible assembly; (c) substantial operational convenience for physicians; (d) substantial time savings for the benefit of both patients and physicians; and (e) quality PTA with comparably less dissections. FICS functional units can save procedural clinical time by enabling convenient interchangeability between different functional units so that physicians can quickly adapt the FICS functional units for each procedural phase, which may vary in procedural complexity depending on the characteristics of a treatable plaque/lesion (in terms of the number and dimensional variability) without the necessity for withdrawing the Support Catheter for each plaque/lesion treated sequentially thereby preventing loss of lesion access. For example, after employing a first hypothetical FICS configuration in a first interventional procedure (i.e., treatment of a first occlusion), the FICS functional units can be reversibly disassembled in order for the functional units to be reassembled into a different configuration for a second subsequent interventional procedure (i.e., treatment of a second occlusion), if necessary, in the same patient. The cycle of dis-assembly and re-assembly may be repeated multiple times as necessary by clinical operators performing simultaneous and/or sequential applications in vivo. The interoperability of FICS functional units involving a pre-deployed FICS Support Catheter means that the SC can remain deployed for enabling: (a) the continuous lesion access throughout the treatment of an affected vessel; and (b) the rapid exchange of other FICS functional units that may be insertable through the SC lumen for treating a second or subsequent lesion present in the same affected vessel, thereby eliminating the need for retracting the SC for repositioning, saving time, and improving operational convenience.

FIG. 2 illustrates two alternative FICS Dilators for intraluminal or extraluminal CTO recanalization. The FICS Dilator can be combined with the FICS Support Catheter to form the FICS "CTO Dilator" configuration, adapted with a suitable "CTO Penetration Tip" 205 in FIG. 2A. FIGS. 6-7 provide a more detailed description of the "CTO Penetration Tip" shown as 205 in FIG. 2A. FIGS. 8-9 provide a detailed description on alternative projectable and steerable dilator tip designs. FIGS. 12 A-B provide additional operational details of the hydraulically actuated mechanism for tip propagation.

FIG. 2A shows an exemplary "CTO Penetration" design adaptable for a FICS CTO Dilator configuration suitable for intraluminal recanalization, as an embodiment. In FIG. 2A, the Functionally Integratable Catheter System (FICS) in the "CTO Dilator" configuration can be assembled together by: (a) attaching the FICS Lock-Grip Handle 230 to the FICS Support Catheter 220; and (b) coaxially inserting the FICS Dilator 210 through the pre-assembled Support Catheter/Lock-Grip Handle described in step (a) so that the "CTO penetration" dilator tip 205 (also shown as 131 in FIG. 1 and explained in further detail in FIGS. 6-8) integrated into the distal end of the FICS Dilator can be positioned and locked length-wise to partially exit from the distal end of the FICS Support Catheter tubing, as shown. When co-assembled with the FICS CTO Dilator, the FICS Support Catheter can facilitate CTO penetration in a pressure and displacement controlled manner.

Figure 5:
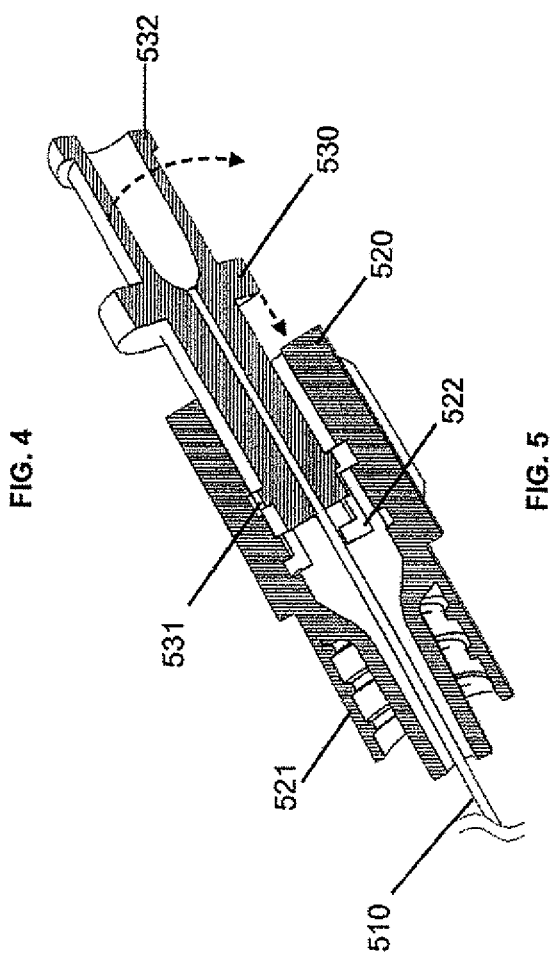
FIG. 5 is a perspective cross-sectional diagram illustrating the internal components of the FICS Steering Hub, as an embodiment.

The FICS Dilator can be combined with the FICS Support Catheter and FICS Steering Hub to form the FICS "Reentry Dilator configuration," adapted with a suitable "Reentry Tip" 206 in FIG. 2B. FIG. 5 provides a more detailed description of the Steering Hub. FIG. 9, 10B provide a more detailed description of the "Reentry" dilator tip 206 of FIG. 2B. FIGS. 12 A-B provide additional operational details of the hydraulically actuated mechanism for tip propagation.

FIG. 2B shows an exemplary "Reentry" design adaptable for a FICS Reentry Dilator configuration suitable for extraluminal recanalization, as an embodiment. In FIG. 2B, the Functionally Integratable Catheter System (FICS) in the CTO Dilator configuration can be assembled together by: (a) attaching the FICS Lock-Grip Handle 230 to the FICS Support Catheter 220; and (b) coaxially inserting the FICS Dilator 210 through the pre-assembled Support Catheter/Lock-Grip Handle described in step (a) so that the "Reentry" dilator tip 206 (part of the dilator tip assembly shown as 131 in FIG. 1 and explained in further detail in FIG. 9) integrated into the distal end of the FICS Dilator can be positioned and locked length-wise to partially exit from the distal end of the FICS Support Catheter tubing, as shown. The dilator tip 206 is attached to the steering hub 250 via coaxially aligned inner elastomeric tubing. When co-assembled with the FICS CTO Dilator, the FICS Steering Hub can facilitate CTO circumnavigation/subintimal access/reentry in a directionally orientable, pressure and displacement controlled manner. The Reentry Tip may be provided for simultaneous use with a designated CTO guide wire, in which the guide wire assumes a CTO penetration function, and the Reentry Tip in conjunction with the FICS Steering Hub assumes a steering function for the GW. In an alternate embodiment, the Reentry Tip in conjunction with the FICS Steering Hub assumes a steering function for GW to facilitate convenient side branch vessel access.

Figure 16:
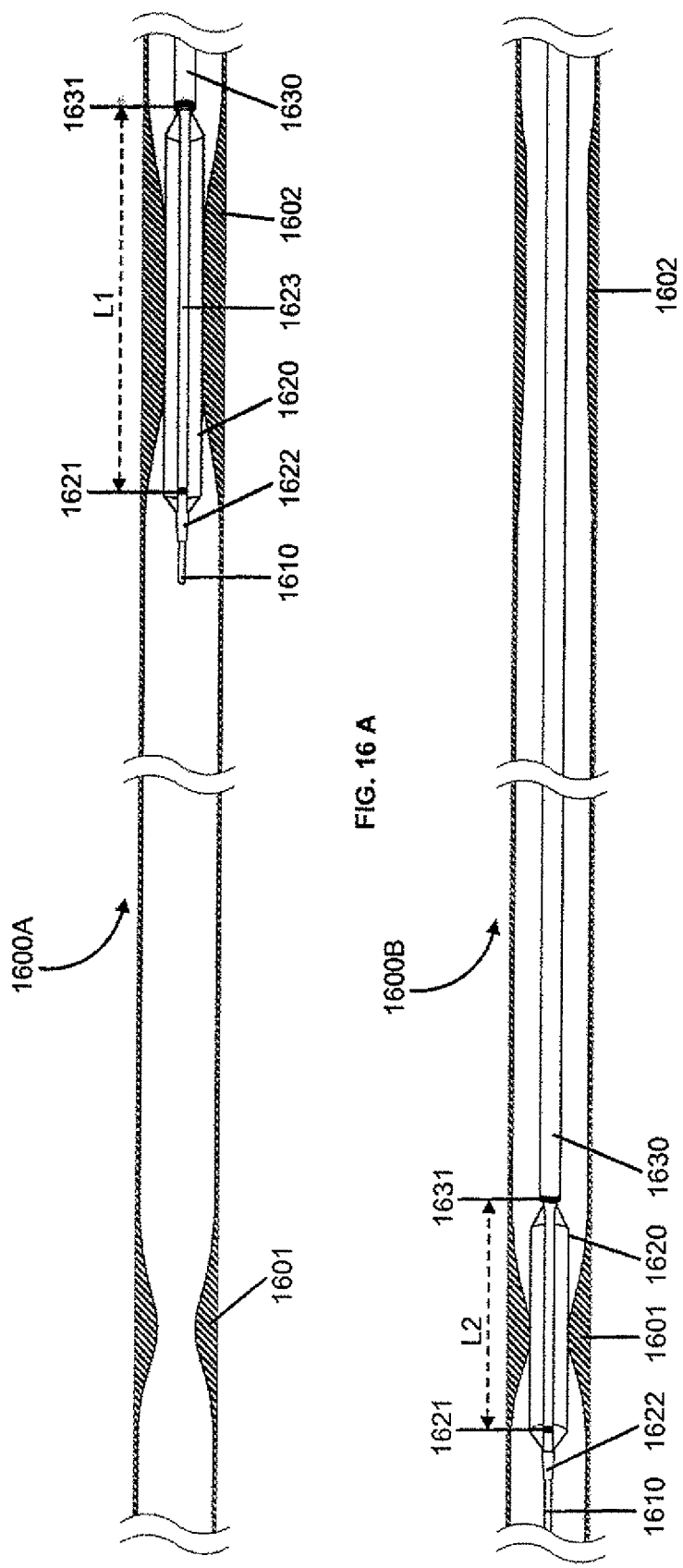
FIGS. 16 A-B illustrate cross-lateral views of the in vivo "lesion-length selective" feature of the inflatable member for the FICS LLS PTA Catheter for successive lesion treatment, as an embodiment.

FIG. 3 shows the assembled "FICS LLS PTA configuration" useful for "lesion-length selectivity," as an embodiment. In FIG. 3, the Functionally Integratable Catheter System in the LLS PTA catheter configuration can be assembled together by: (a) attaching the Lock-Grip Handle 330 to the FICS Support Catheter 320; and (b) coaxially inserting the FICS PTA Catheter 310 through the pre-assembled Support Catheter/Lock-Grip Handle described in step (a) so that the inflatable member 305 (also feature 141 in FIG. 1 and explained in further operational detail in FIGS. 12, 13), distally integrated into the PTA Catheter 310, can be positioned and locked length-wise to distally expose the inflatable member 141 to an adjustable length as desired. In this configuration, the length of the exposed inflatable member 305 represents the "lesion-length selective" portion of the FICS LLS PTA Catheter configuration as described herein. When co-assembled with the FICS Support Catheter, the balloon length can be specifically adjusted in vivo to be adequately proportional to the target lesion length, enabling effective lesion treatment and improved lesion access with less procedural steps. By adjusting balloon length and appropriate inflation pressure, physicians can deploy a very flexible, high quality PTA balloon specifically suitable for the length and texture of a hypothetical lesion. Thus, the adjustable FICS configurations can increase the quality of the treatment, resulting in reduced risk of dissections, increased procedural efficacy, reduced procedural time and cost. In this configuration, the FICS Lock-Grip Handle 320 can stabilize the position of the outer sheath formed by the FICS Support Catheter 310 relative to the position of the FICS LLS PTA Catheter by preventing proximal movement (recession) of the FICS Support Catheter 310 during balloon dilatation. FIGS. 11, 14 and 16 provide additional operational details of the "FICS LLS PTA" configuration.

1.3 an Overview of Multiple FICS Configurations that can be Selectively Configured by Clinicians FIG. 17 is a flow-chart overview of the possible FICS System "configurations" as contemplated herein, providing a visual map of the various "functional units" and "functional subunits" that can be selectively combined by a clinical operator for constructing therapeutic-specific "configurations" most effective for treating a broad range of complex lesions and CTOs. Solid framed boxes and solid arrows of FIG. 17 indicate combinations of "functional units" and "functional subunits" that can be effective for a given therapeutic application. The dashed boxes and dashed arrows included in FIG. 17 indicate alternative combinations of "functional units" and "functional subunits" that may be configurable, if suitable for a given clinical situation.

In FIG. 17, the flow chart indicates certain therapeutic-specific "configurations" that can be selectively assembled by clinical operators as suitable for patient-specific situations. Starting at the top left of the diagram, 1700 represents the FICS System, resulting from the selective configurations (1710) of various "functional units" (1720) and "functional subunits" (1730) that can be assembled together by clinical operators. The three main FICS configurations in alignment with 1710 are shown as solid boxes: 1711 representing the "FICS LLS PTA configuration" (FIG. 3); 1712 representing the "FICS CTO Dilator configuration" (FIG. 2A); and 1713 representing the "FICS Reentry Dilator configuration," respectively from top down.

The "FICS LLS PTA configuration" 1711 can be configured by combining the following three main functional units represented as "solid" boxes: Support Catheter 1721, PTA Catheter 1723 and Lock-Grip Handle 1724 (individual functional units as illustrated in FIG. 1; configured in FIG. 3). The Dilator 1722 and the Steering Hub 1725 are represented by dashed boxes to indicate that these functional units may be temporarily employed during the maneuvering of the Support Catheter 1721 and/or they may be optionally included for user convenience. For example, the Dilator 1722 can be inserted into the Support Catheter 1721 (stabilized by the Lock-Grip Handle 1724) for effecting atraumatic maneuvering of the Support Catheter over the GW prior to administering the "FICS LLS PTA configuration."

The "FICS CTO Dilator configuration" 1712 can be configured by combining the following three main functional units represented as "solid" boxes: Support Catheter 1721, PTA Catheter 1723 and Lock-Grip Handle 1724 (individual functional units as illustrated in FIG. 1; configured in FIG. 2A). The PTA Catheter 1723 and the Steering Hub 1725 are represented by "dashed" boxes to indicate that these functional units are optional (e.g., suitable during the deployment of the Dilator configuration). The PTA Catheter 1723 (shown as a dashed box) is not part of the Dilator configuration because the PTA deployment becomes applicable only after achieving CTO penetration. Because the "FICS CTO Dilator configuration" for achieving intraluminal CTO penetration generally involves direct penetration of the CTO, the steerability of the Steering Hub 1725 (shown as a dashed box) (as illustrated in FIG. 5; configured as 1736) can be optionally selected if suitable. In addition to selecting these main functional units, the clinical operators may select from several FICS Dilator designs options, each incorporating a unique distal tip design suitable for a given therapeutic application, by selecting from these options for constructing "CTO Penetration Tips": (a) an inflatable dilator tip 1734 capable of anchoring and centering; and (b) a non-anchoring/non-centering (without an inflatable member) dilator tip 1735. Furthermore, the clinical operators may select from several dilator tip designs, each comprising a hypotube tip (formed as a lancet) having either a "non-steerable," blunt-ended single member 1741 (FIG. 8,10A), or a "steerable" conjoined member 1743 (FIGS. 9, 10B) to configure a therapeutic-specific FICS configuration suitable for patient-specific situations. Furthermore, the FICS Dilator incorporating a "CTO Penetration Tip" 1742 (as illustrated in FIGS. 6-8, 10A) can be conjoined with other functional units such as the Support Catheter and the PTA Catheter for constructing a therapeutic-specific configuration capable of intraluminal recanalization.

The "FICS Reentry Dilator configuration" 1713 can be configured by combining the following three main functional units represented as "solid" boxes: Support Catheter 1721, PTA Catheter 1723 and Lock-Grip Handle 1724 (individual functional units as illustrated by FIG. 1; configured in FIG. 2B). The PTA Catheter 1723 represented by a dashed box is an optional functional unit. Clinical operators may select from several FICS Dilator designs options, each incorporating a unique distal tip design suitable for a given therapeutic application, by selecting from these options: (a) an inflatable dilator tip 1734 capable of anchoring and centering; and (b) a non-anchoring/non-centering dilator tip (without an inflatable member) 1735. Furthermore, the dilator tip comprising a hypotube tip (formed as a lancet) having either a non-steerable, single member 1741 (FIG. 8), or a steerable conjoined member 1743 (FIG. 9), may be further selected to configure a therapeutic-specific FICS configuration suitable for patient-specific situations. The Steering Hub 1725 (as illustrated in FIG. 5; configured as 1736) is further required to controllably manage the steerable conjoined member 1743 (FIG. 9). Furthermore, the FICS Dilator incorporating a "CTO Penetration Tip" 1742 (as illustrated in FIGS. 6-8) can be conjoined with other functional units as the Support Catheter and the PTA Catheter. The FICS Dilator incorporating a "Reentry Tip" 1745 (as illustrated in FIGS. 9, 10B) can be conjoined with other functional units such as the Support Catheter and the PTA Catheter (as illustrated in FIG. 1) for constructing a therapeutic-specific configuration capable of extraluminal recanalization.

The "FICS Dilator," as part of the FICS System, can be provided as a therapeutically effective implement for performing intraluminal and/or extraluminal recanalizations for performing lesion length selective, multi-stage dilations, wherein the manufacture can provide several alternative designs for the Dilator by incorporating various subunits for constructing the therapeutic-specific dilator tip portions, such as: (a) a non-inflatable, distal polymeric member without anchoring and/or centering functionality; (b) an inflatable, distal polymeric member exhibiting anchoring and/or centering functionality; (c) a hydraulically actuated, hypotube tip coaxially embedded into at least a portion of the distal polymeric member, capable of translational movement; (d) a hydraulically actuated, hypotube tip coaxially embedded into at least a portion of the distal polymeric member, capable of translational and rotational movement; wherein the inner tubular member member can be provided conjoinable to a steering hub; and wherein the hypotube distal tip portion can be formed either as a "CTO penetration Tip" or a "Reentry Tip" or as a tip conferred with the functionalities of both of these. As further embodiment, the inflatable, polymeric member (b) can be formed by combining: (i) Support catheter and (ii) PTA catheter. As a related embodiment, "CTO Dilator" and/or "Reentry Dilator" configurations may be formed by utilizing: a) Support Catheter; b) PTA catheter; c) Lock-Grip; and d) Hypotube formed with respective "CTO Penetration Tip" and/or "Reentry Tip", wherein the PTA catheter comprises a hydraulic chamber for actuation of the hypotube member coaxially receivable therein.

2. FICS Functional Units 2.1 FICS Lock-Grip

FIG. 4 is a perspective diagram illustrating the internal components of the FICS Lock-Grip Handle, as an embodiment. In FIG. 4, the FICS Lock-Grip Handle comprises (from left to right): a proximal connector element 411, joined with a first casing member 420, a compressible seal 421, and a second casing member (shaft-locking handle) 430 joined with a distal connector element 431, wherein these components can be connected as shown to enable operability. The first casing member 420 can be coupled/connected to the second casing member (a shaft-locking handle) 430 via threaded surface portions 412, 432 to achieve operational coupling.

The FICS Lock-Grip Handle is an essential component of the FICS Dilator configuration (as shown in FIG. 2), and the FICS LLS PTA Catheter configuration (as shown in FIG. 3) by enabling the shaft member of either FICS Dilator or FICS LLS PTA Catheter to be coaxially engaged with respect to the FICS Support Catheter so that the distal tips of either functional units can be projected controllably in vivo through the distal end of the FICS Support Catheter towards a target occlusion/plaque/lesion for successful circumnavigation/penetration/crossing. The FICS Lock-Grip Handle can mechanically engage/disengage the shaft portion of either FICS Dilator or FICS LLS PTA Catheter so that relative translational movement and positioning of these components with respect to the FICS Support Catheter can be enabled. The FICS Lock-Grip Handle provides hemostatic sealing across the outer shaft portion to prevent excessive bleeding during device operation.

A shaft member of the FICS Dilator or FICS LLS PTA Catheter can attach reversibly to the Lock-Grip casing members 420 and 430 via the compressible seal 421 contained within the Lock-Grip Handle. To completely remove the FICS Dilator or FICS LLS PTA Catheter, the Lock-Grip Handle can be un-locked (disengaged) and the shaft can be pulled out of the Support Catheter, for example, after the completion of a CTO recanalization procedure. The independent integration of a FICS Dilator based on a hydraulic tip-actuation mechanism and a Lock-Grip Handle based on a shaft-locking mechanism enables the operation of a single integrated device: (a) to independently facilitate hemostatic sealing in order to control/restrict blood flow through the treated vessel during the interventional procedure; (b) to mechanically engage/lock the shaft member to the FICS Support Catheter; (c) to hydraulically project the dilator tip into the target occlusion/plaque/lesion; and (d) to transport fluid through the affected vessel to diagnostically visualize the interventional outcome and/or to effect adjunct therapies. The FICS Lock-Grip can be maintained at the proximal hub section of the FICS Support Catheter throughout the intervention stages.

2.2 FICS Steering Hub

FIG. 5 is a perspective cross-sectional diagram illustrating the internal components of the FICS Steering Hub, as an embodiment. In FIG. 5, the FICS Steering Hub comprises (from left to right): a proximal connector element 521, joined with a first casing member 520, having bayonet-type surface grooves 522 oriented along its inner surface, and a second casing member 530 joined with a distal connector element 532, having matching outer surface protrusions 531, wherein these components can be connected as shown to enable operability. The first casing member 520 can be coupled/connected to the second casing member 530 via the guiding surface structures to achieve operational coupling. Further, an elastomeric tubing 510 (item 940 of FIG. 9), which is further adjoined with the Dilator tip (item 910 of FIG. 9) can be provided attached to the second casing member 530.

The second casing member 530 can be moved along the surface grooves 522 of the first casing member, from a freely rotatable, first extended position, along the longitudinal groove sections into one or more rotation-locked and translation-locked, consecutive, contracted positions. In FIG. 5, a total of four individual guiding channels can be placed at 90° angles with respect to each other. By arrangement of the guiding surface channels as shown, the second member can be translationally displaced from a first extended position to one or more consecutive, contracted positions while allowing the second casing member to assume one of four rotational orientations within the range of 0°, 90°, 180°, and 270°. Through operation of the second casing member, the relative translational and rotational movements (as indicated by dashed arrows) can be directly exerted onto the dilator tip. FIGS. 6, 7 and 9 provide additional embodiments/details for dilator tip configurations utilizing the Steering Hub.

The FICS Steering Hub is an essential component of the FICS Dilator configurations (as shown in FIG. 2A-B), by enabling the tip member of either FICS "FICS Reentry" configuration or the FICS "CTO Dilator" configuration to be coaxially engaged with respect to the FICS Support Catheter so that the distal tips of either functional units can be directionally guided and controllably projected in vivo through the distal end of the Support Catheter towards subintimal tissue near the target occlusion/plaque/lesion for successful circumnavigation/penetration/crossing. The FICS Steering Hub can mechanically engage/disengage the tip portion of either FICS Reentry configuration or FICS CTO Dilator configuration so that relative translational movement and rotational orientation of these components with respect to the FICS Support Catheter can be enabled.

2.3 FICS Dilator and Tip Configurations

The FICS Dilator can be provided preconfigured with various features enhancing the convenient operability of the FICS Dilator in designated functional configurations. The respective tip configurations are described in detail hereafter. The FICS Dilator can be provided with or without anchoring/centering functionality shown in FIGS. 6-7. Furthermore, the projectable tip portion can be provided with or without steering functionality as shown in FIGS. 8-9. The FICS Dilator can be provided as a "CTO Dilator" or as a "Reentry Dilator," depending on the tip configuration. As an embodiment, the FICS Support Catheter can be combined with the FICS Dilator to form a FICS "CTO Dilator," having "CTO Penetration Tips" (FIGS. 6-8 and FIG. 10A) capable of performing intraluminal recanalization. As another embodiment, the hypotube body that can be distally shaped as "CTO Penetration Tips" (FIG. 10A, shown in FIG. 6-8) can be replaced by a hypotube body adapted with a "Reentry Tip" (FIG. 10B, shown in FIG. 9) to yield a "FICS Reentry Dilator" configuration shown in FIG. 2B, capable of performing extraluminal recanalization via subintimal access and reentry.

In general, the FICS Dilator can be designed to include at least: (a) a specifically configured, hydraulically projectable tip constructed from a concentrically positioned hypotube to facilitate enhanced intra- and/or extraluminal recanalization of chronic total occlusion; and (b) a tapered, polymeric sleeve or shaft portions to provide a seamless transition from the guide wire to the distal end of the FICS Support Catheter for enabling enhanced, atraumatic passage, guidance and support. The FICS Dilator is configured for inter-operability with the FICS Support Catheter, which can provide substantial structural guidance and support as an external tubular shield. With respect to the exemplary FICS Dilator tip configurations described below in FIGS. 6-10, these FICS Dilator tips can remain receded within the GW lumen compartment of the FICS Dilator seated within the FICS Support Catheter to shield the vessel walls during transport and maneuvering operations, thereby avoiding potential vessel damage.

2.3.1 Anchoring/Non-Anchoring Variations of FICS Dilators

FIG. 6 illustrates a cross-sectional view of a hydraulically actuated "CTO Penetration Tip" with anchoring and/or centering functionality that can be incorporated into the distal tip of a FICS Dilator, as an embodiment. In FIG. 6, the "CTO penetration" dilator tip 610 can be coaxially/concentrically aligned within a triple lumen radially expandable polymer member 620 having an actuation lumen 621 and an inflation lumen 622, wherein the tip portion formed by 610/620 members can exhibit an expandable diameter. The tip portion 610/620 of the FICS Dilator can exit from the distal end of the FICS Support Catheter 630 as shown. A hydraulic chamber 625 can be formed between the proximal lateral surface of a distal seal/gasket 611, the distal lateral surface of a proximal seal/gasket 612, the internal surface of an elongated tubular member forming the dilator shaft, and the external surface of a hypotube member 610 coaxially received therein. The distal seal/gasket can extend from the external hypotube surface. The proximal seal/gasket can extend from the inner surface of the elongated tubular member.

In another embodiment, the CTO penetration dilator tip comprises a hypotube segment coaxially received within an outer dilator shaft surface, and is operationally coupled to a hydraulically actuated tip propagation mechanism to controllably advance the hardened tip into the CTO cap region through relative translational movement along the length axis of the dilator shaft. The actuation mechanism can be configured for controllable, bi-directional tip propagation. The dilation tip itself can be embedded into or encapsulated with a tapered polymeric sleeve, to gradually align the circumferential diameter to the circumference of the dilator shaft, in order to enable a seamless transition. The tip and distal shaft segment of the FICS CTO Dilator can be configured to be directionally shapeable. The dilator shaft can be manufactured from a single lumen polymeric sleeve shaft, or from a dual-lumen or multi-lumen polymeric shaft, in order to provide a FICS CTO Dilator that can incorporate reversibly inflatable dilation elements for temporary vessel centering and anchoring means.

This expandable configuration in FIG. 6 can be adjusted to fit vessels of variable diameters and lengths. When inflated, the radially expandable polymer member 620 can serve as "anchoring" and "centering" balloon for improving vessel-anchoring capability for effective coaxially aligned (head-on) penetration of the hydraulically actuated "CTO penetration" dilator tip and consecutive guide wire passage through the CTO. Alternatively, such an anchoring "CTO Penetration Tip" configuration can be provided through simultaneous combination of a coaxially insertable hypotube element and the inflatable member of the FICS LLS PTA catheter (not shown). FIGS. 8-9 provide detailed descriptions for projectable and steerable tips. FIGS. 12 A-B provide additional operational details of the hydraulically actuated mechanism.

FIG. 7 illustrates a cross-sectional view of a hydraulically actuated "CTO Penetration Tip" without anchoring and/or centering functionality that can be incorporated into the distal tip of a FICS Dilator, as an embodiment. In FIG. 7, a basic non-anchoring dilator type can be formed by providing a "CTO Penetration Tip" 710 coaxially/concentrically aligned within a dual lumen non-inflatable polymer member 720 having an actuation lumen 721, wherein the tip portion formed by 710/720 exhibits a constant circumference (along a defined tip length portion). The tip portion 710/720 of the FICS Dilator can exit from the distal end of the FICS Support Catheter 730. The basic "CTO Penetration Tip" can be formed as a polymeric body 720 of oblong shape, comprising a distal, tapered tip portion and having a length section of uniform radial circumference adapted fittingly receivable within an outer support catheter sleeve 730, as shown. A hydraulic chamber 725 is formed between the proximal lateral surface of a distal seal/gasket 711, the distal lateral surface of a proximal seal/gasket 712, the internal surface of an elongated tubular member forming the dilator shaft, and the external surface of a hypotube member 710 coaxially received therein. The distal seal/gasket extends from the external hypotube surface, whereas the proximal seal/gasket extends from the inner surface of the elongated tubular member. FIGS. 8-9 provide additional details on dilator tip cross-sectional subassemblies for enabling projectable and steerable tip assembly configurations, whereas FIGS. 12 A-B provide additional operational details of the hydraulic actuation mechanism.

2.3.2 Non-Steerable/Steerable Tip Variations for FICS Dilators

FIG. 8 illustrates a lateral view of a hydraulically actuated, non-steerable distal tip portion of a FICS Dilator, capable of translational movement along the longitudinal axis, as an embodiment. In FIG. 8, the hydraulically actuated, non-steerable tip of the Dilator is detachable to a Steering Hub. The tip member 810 can be formed from a hollow bore hypotube, having a circumferentially affixed distal gasket 820 capable of sealing and sliding while embedded into a hydraulic lumen section of the polymeric dilator tip portion disclosed in FIGS. 6-7. The dilator tip 810 comprises a second proximal gasket 830 that can act as a mechanical end stop that can limit the longitudinal extension of the hydraulically actuated tip member beyond a certain length threshold. The inner surface profile of the proximal gasket can be tapered to allow for a seamless transition between the internal lumen diameter of the hollow Dilator tip portion and for the guide wire lumen diameter to extend across the complete tip, thereby facilitating efficient and unrestricted guide wire passage through both lumens. The non-steerable hypotube tip can be embedded within the hydraulic chamber as a singular, unaffixed and freely movable member within the boundaries defined through the respective gasket position(s) and chamber dimensions. The gasket opening situated proximally on the hypotube tip (lancet) may be formed with a tapered surface profile relative to the GW lumen of the Dilator, so that any guidewires may seamlessly pass through and across the GW lumen portion formed within the hollow hypotube tip (lancet) in a considerably unrestricted manner. The tip member 810 can be provided as a "CTO Penetration Tip" or "Reentry tip." FIGS. 12 A-B provide additional operational details of the hydraulically actuated mechanism.

FIG. 9 illustrates a lateral view of a hydraulically actuated, steerable distal tip portion of a FICS Dilator, capable of translational movement and rotational movement about the longitudinal axis, as an embodiment. In FIG. 9, the hydraulically actuated, steerable tip of the Dilator is attachable to a Steering Hub. The tip member 910 can be formed from a hollow bore hypotube, having a circumferentially affixed distal gasket 920 capable of sealing and sliding while embedded into a hydraulic lumen section of the polymeric dilator tip portion disclosed in FIGS. 6-7. The steerable tip member 910 contains a second proximal gasket 930 that can act as a mechanical end stop that can limit the longitudinal extension of the hydraulically actuated tip member beyond a certain length threshold. The proximal gasket can serve as the distal receiving end for an elastomeric tubing member 940 that can be attached to the proximal steering hub to allow for directional steering of the tip member 910. The tip member 910 can be provided as a "Reentry Tip" or "CTO Penetration Tip." FIG. 5 provides further details on the proximal attachment and steering means via the tubing member 940 (equivalent to item 510 of FIG. 5). In the steerable configuration, the hypotube tip (formed as a lancet) can be longitudinally displaced (extended/retracted) through hydraulic actuation (within a length range definable through the respective gasket position(s) 910/920 acting as mechanical end stops in relation to the hydraulic chamber lumen length). The lancet can be conjoined to the FICS Steering Hub via an elastomeric tubing attachable to a portion of the proximal gasket and a member portion of the steering hub (the second casing member) in order to confer an adequate degree of directional steerability (rotation) to the lancet itself. FIGS. 12 A-B provide additional operational details of the hydraulically actuated mechanism.

2.3.3 FICS "CTO Penetration" and "Reentry TIP"

FIGS. 10 A-B provides exemplary dilator tip designs for facilitating intraluminal and extraluminal recanalization. FIG. 10A is a magnified view of a "CTO Penetration Tip" comprising a non-malleable and blunt-ended hypotube of a FICS Dilator suitable for intraluminal recanalization, as an embodiment. In FIG. 10A, the "CTO Penetration Tip" of FIG. 6-8 can be formed from a hollow-bore hypotube, having a substantially elongated tubular member 1030 and a blunt-edged tip 1011, as shown. The CTO Penetration Tip can be formed from a combination of one or more substantially rigid ceramic, polymeric or metal based materials to enable puncture and subsequent penetration of hardened, calcified CTO cap regions, wherein the tip can be independently formed as or be jointly affixed to a hypotube to further increase pushability while preventing or reducing any potential bending, buckling or kinking of the distal dilator shaft segment during CTO penetration. The FICS Dilator adapted with a "CTO Penetration Tip" is suitable in clinical situations in which direct CTO passage (utilizing the FICS Dilator adapted with a "CTO Penetration Tip") for effecting intraluminal recanalization may be desired.

FIG. 10B is a magnified view of a "Reentry Tip" comprising a malleable and angled hypotube of a FICS Dilator, suitable for extraluminal recanalization, as an embodiment. In FIG. 10B, the "Reentry Tip" of FIG. 9 differs from the "CTO Penetration Tip" (FIGS. 6-8 and FIG. 10A) particularly by the incorporation of a substantially malleable hypotube segment 1020 that can be precisely cut (as slotted-tube or in a spiral pattern) into the hypotube member 1020 and positioned in close proximity to the distal tip portion 1013. The FICS Dilator adapted with a "Reentry Tip" is suitable in clinical situations in which direct CTO passage (utilizing the FICS Dilator adapted with a "CTO Penetration Tip") may be unsuitable. A FICS Dilator adapted with a "Reentry Tip" can be utilized in preparation for percutaneous intentional extraluminal recanalization, referred to as a "reentry procedure," which involves the following steps: (a) creating a directional cut into the subintimal tissue layer in proximal vicinity of a target CTO; (b) crossing the formed opening with a guide wire; (c) creating a directional cut into the subintimal tissue layer in distal vicinity of the CTO; (d) crossing the formed opening with a guide wire so that the CTO can be extraluminally circumnavigated; (e) performing a reentry into the true lumen of the vessel; (f) dilating the artificially formed extraluminal passage; and (g) restoring perfusion through the affected vessel. The exposable hypotube tip (lancet) section can be provided with a straight, angled, or shapeable tip orientation. The hypotube flexible tip may be initially provided, which can be further manipulated ex vivo into a particular shape of interest by the physician, for example by utilizing a pre-shaping tool, and loaded (retracted) in a pre-tensioned state into the Dilator/LLS via coaxial arrangement. By exposing the pre-tensioned segment, for example by mechanical tip propagation, the tip can assume the pre-shaped configuration in vivo to facilitate optimized subintimal tissue penetration. The tip/shape can be formed out of a plastically/elastically deformable metal alloy. Alternatively, beneficial shape memory effects can be utilized by forming the tip out of a pseudoelastic or superelastic alloy, such as Nitinol. The edge of the distal tip can be formed through precision cutting and polishing, variably angled, for example, obtusely or acutely angled relative to the length axis, to achieve a variably blunt or sharp tip, for improved shaft pushability and capability for efficiently cutting into the subintimal tissue layer in a directionally guidable manner.

In general, the hydraulically projectable hypotube tip sections can be provided with a straight, angled, or malleable tip. The edge of the distal tip can be formed through processes of precision cutting and polishing, or can be variably angled (e.g., obtusely or acutely angled relative to the length axis) to achieve a variably blunted or sharpened tip for improving shaft pushability, directional control, and cutting efficiency into CTO and/or subintimal tissue during penetration. An an embodiment, the flexible reentry tip can be blunt-edged to minimize the risk of vessel perforation during subintimal access. In another embodiment, the CTO penetration tip may be provided with a flexible segment to enable simultaneous CTO penetration and/or reentry capability. The inner tubular member forming the hypotube may comprise a combination of metals and polymers as indicated throughout the specification.

3. Operational Characteristics of the FICS System
3.1 FICS LLS PTA Dilator Configurations Capable of Lesion-Length Selectivity for Multi-Staged Procedures FIG. 11 is an exemplary flow diagram of a multi-staged angioplasty procedure performed in vivo for successive therapeutic treatment of complex lesions and CTOs utilizing the FICS System, as one embodiment. In FIG. 11, as the first step 1101, an introducer sheath can be inserted to enable vascular access of catheter devices under hemostatic conditions. In step 1102, the predisposed guide wire can be controllably advanced to the target treatment area and positioned across the lesion. In step 1103, the FICS Support Catheter can be inserted simultaneously with the FICS Dilator through the lumen of the introducer sheath and over the predisposed guide wire. In step 1104, the FICS Support Catheter and FICS Dilator can be controllably and simultaneously advanced over the prepositioned guide wire to the first intended treatment area, such as a first hypothetical complex lesion. In step 1110, the FICS Dilator tip (also "CTO Penetration Tip") can be controllably advanced into the hardened surface cap of a CTO to facilitate guide-wire negotiation and CTO penetration. In step 1111, the FICS Dilator can be retracted, and the FICS PTA Catheter can be inserted. In step 1112, the FICS PTA Catheter can be controllably advanced via the predisposed FICS Support Catheter and over the predisposed guide wire to a first, complex lesion. In step 1113, the distal working end of the formed FICS LLS PTA Catheter can be utilized to "length-selectively" treat the lesion and restore luminal patency at the first intended treatment site. This step enables the angiographic visibility of lesions distally located in the affected vessel. After deflating and retracting the length selective balloon element back into the FICS Support Catheter in step 1121, the flushing holes of the FICS Support Catheter can be used for injecting contrast agent to enable angiographic follow up. As an optional step 1122, if additional lesions may be observable along the same affected vessel, the usable length portion of the FICS LLS PTA Catheter can be manually extended by the physician while maintaining the current position of the guide wire within the intended treatment site. The predisposed guide wire can be controllably advanced to the next target treatment area and the distal end of the guide wire across the second lesion can be positioned. In step 1123, the physician can controllably advance the optionally extended FICS LLS PTA Catheter together with the FICS Support Catheter over the prepositioned guide wire to the next intended treatment area, such as a second lesion. In step 1124, the distal working end of the optionally extended FICS LLS PTA Catheter can be utilized to treat the lesion and restore luminal patency at the second intended treatment site. The number of treatment sites utilized in this flow diagram is exemplary in nature and can include an arbitrary number of successive treatment sites provided that the length of the predisposed guide wire, the length of the support catheter, and the adjustable usable length portion of the catheter in extended configuration enables access to successive target treatment areas.

3.2 Dilator-Tip Propagation Mechanisms

FIG. 12 illustrates a cross-sectional view of a hydraulic-actuated dilator tip propagation mechanism in retracted form (FIG. 12A) and extended form (FIG. 12B), and a three-lumen dilator shaft (FIG. 12C). In FIG. 12A, as one embodiment of the present disclosure, a hydraulic dilator tip actuation mechanism 1200A in retracted condition is shown. The tip actuation mechanism comprises a hydraulic chamber, formed between the proximal lateral surface of a distal seal 1262, the distal lateral surface of a proximal seal 1261, the internal surface of an elongated tubular member 1210 forming the dilator shaft, and the external surface of a hypotube member 1222 coaxially positioned. The distal seal extends from the external hypotube surface. The proximal seal extends from the inner surface of the elongated tubular member. The interstitial space formed is shown in fluid communication with a hydraulic lumen 1231, whereby the delivery of fluid to the interstitial space as indicated by the dashed arrow can project the dilator tip portion distally. A mechanical end stop 1263 can be provided extending from the hypotube shaft at a designated proximal position relative to the proximal seal to prevent the inadvertent extension of the tip beyond a defined length section. Alternatively, the mechanical endstop functionality can be provided through the distal seal 1262. The distal dilator tip portion 1220, embodied with a cutting edge to enable enhanced CTO lesion penetration, and formed from the hypotube body 1222, can be coaxially receivable within the distal section of the elongated tubular member. The elongate tubular member 1210 forming the dilator shaft can be provided as a three-lumen polymeric body, comprising a hydraulic lumen 1231, an inflation lumen 1241 and a hypotube or guide wire lumen 1260. An optional inflatable member 1250 is shown in fluid communication with the inflation lumen as indicated by a dashed arrow to facilitate in- and/or deflation of the inflatable member prior to tip extension to provide for vessel centering and anchoring means. The hypotube can be configured as a single lumen metal tube dimensioned to facilitate guide wire passage. In FIG. 12A, the tip portion is maintained in a first retracted condition concentrically concealed within the tubular member to prevent any vessel injury during dilator movement. The FICS Dilator is intended to move within the lumen of a stationary FICS Support Catheter positioned as a supportive guiding sleeve (not shown).

In FIG. 12B, a hydraulically actuated dilator tip propagation mechanism in fully extended condition is shown. Upon actuation of the distal dilator tip section via hydraulic means, the distal dilator tip portion 1220 can be extended beyond the lateral opening of the elongate tubular member 1210 to enable lesion penetration. The individual stages of lesion penetration in conjunction with the support catheter are further illustrated in FIG. 13.

In FIG. 12C, the cross-sectional profile along the defined distance A-A (shown in FIG. 12A) provides a detailed illustration of a three-lumen Dilator shaft. The elongate tubular member 1210 forming the dilator shaft is shown configured as a three-lumen polymeric body, comprising a substantially concentric hydraulic lumen 1231, an inflation lumen 1241 and a hypotube or guide wire lumen 1260. A polymeric sheath 1223 concentrically positioned around the hypotube member can be further included to provide a connection to the Steering Hub as described in FIG. 5.

3.3 CTO Penetration by Dilator Tip Propagation

FIGS. 13 A-D illustrate cross-lateral views representing four consecutive configurational stages A-D for hydraulically propagating the "CTO Penetration Tip," as an embodiment. In FIG. 13A, a cross-lateral view of an occluded vessel 1300 amenable for treatment is shown at the first hypothetical stage, including a vessel wall 1301, a hardened CTO lesion cap 1302 and softer lesion tissue 1303. FICS Support Catheter 1310 is illustrated as an elongated tubular member concentrically situated in the affected vessel and positioned along the vessel length axis 1344, and can incorporate a radiopaque marker band 1311 located on a distal tip region, and one or more proximally positioned flushing/aspiration holes 1312, 1313, and 1314. The FICS Dilator can be inserted concentrically within the lumen space of the predisposed and temporarily stationary FICS Support Catheter shaft 1310, and can be longitudinally positioned with respect to the length axis of the FICS Support Catheter, so that a proximal radiopaque marker 1326 located on the FICS Dilator shaft 1320, and an inflatable member 1330, can be positionally aligned with a substantially similarly sized radiopaque marker 1311 located near the distal end of the FICS Support Catheter. Alternatively, a differently sized radiopaque marker 1325 proximately near the tapered, distal dilator tip portion 1321, and one or more of the radiopaque markers 1311 can be aligned to indicate adequate tip positioning and proper atraumatic alignment between the FICS Support Catheter and FICS Dilator, if desired. At this stage, it is noted that inflatable member 1330 is substantially folded within the FICS Support Catheter.

In FIG. 13B, the cross-lateral view of an occluded vessel 1300 amenable for treatment is shown at the second hypothetical stage, wherein the FICS Dilator shaft 1320 can be transposed distally in parallel with the length axis of the FICS Support Catheter 1344 and positioned in close proximal contact with the lesion cap 1302. The relative positions for FICS Dilator and FICS Support Catheter can be angiographically verifiable by the equidistant positioning of the three radiopaque markers 1311, 1325, and 1326 and the radiopaque penetration tip. Additionally, in this position, the radiopaque marker position 1325 can congruently align with the distal end of the equally fluoroscopically visible tip, indicating to the physician that the tip is safely sheathed inside the dilator tip. At this stage, the inflatable member 1330 of the FICS Dilator in an uninflated state can be exposed/unsheathed in distal direction from the FICS Support Catheter 1310, as shown.

In FIG. 13C, the cross-lateral view of an occluded vessel 1300 amenable for treatment is shown at the third hypothetical stage, wherein the inflatable member 1330 of the FICS Dilator can be inflated for vessel centering and anchoring in preparation for CTO penetration. Once anchored radially into the vessel, the "CTO penetration" distal tip 1341 of the FICS CTO Dilator can be fully extended distally, conferred by the hydraulic-actuation mechanism described in FIG. 12 in order to penetrate the hardened lesion cap 1302 in preparation for guide-wire negotiation.

In FIG. 13D, the cross-lateral view of an occluded vessel 1300 amenable for treatment is shown at the fourth hypothetical stage, wherein the penetrated lesion cap 1302 can be negotiated with a guide wire 1350 to facilitate guide wire crossing across the remaining lesion in preparation for lesion dilation.

3.4 Lesion Length Adaptibility for Successive Multi-Stage Treatment

FIGS. 14 A-D illustrate the inter-operability of the functional units for enabling in vivo "lesion-length selectivity" and deploying the FICS LLS PTA configuration in successive multi-level stages, as an embodiment. In FIG. 14A, the PTA Catheter 1412 can be coaxially inserted into the FICS Support Catheter shaft 1420 through the associated support catheter hub 1421 and via the attached FICS Grip-Lock Handle 1430. The distal tip portion 1410 of the FICS PTA Catheter can exit from the distal end of FICS Support Catheter shaft 1420 to form a seamless transition with the catheter shaft. The relative position between the FICS PTA Balloon Catheter and the FICS Support Catheter end can be dialed-in using the mechanical locking feature of the Lock-Grip Handle 1431 and the surface markings 1411 placed on the proximal FICS PTA Catheter shaft. The Lock-Grip Handle 1431 can be mechanically engaged (screwed shut via the hemostatic valve seal 1431) to lock the current position of the formed FICS LLS PTA Catheter tip to ensure atraumatic passage of the FICS components along affected vessels. The configuration shown in FIG. 14A is optimal for advancing the distal tip of FICS to the target treatment site.

In FIG. 14B, the FICS Lock-Grip Handle can be disengaged (the hemostatic valve screw/seal 1431 is convertible to an open position as indicated by the dashed arrow) to facilitate the lengthwise distal propagation of the FICS PTA Catheter through the FICS Lock-Grip Handle and FICS Support Catheter. In FIG. 14C, the FICS Lock-Grip Handle can be reversibly engaged to lock the selectively exposed length portion of the inflatable member 1450. The configurations shown in FIG. 14B/14C are optimal for in vivo length selective adjustment of the inflatable member portion of the FICS LLS PTA Catheter at the target treatment site. In FIG. 140, the FICS LLS PTA Catheter can be inflated along the pre-dialed exposed length portion, as shown. The configuration shown in FIG. 14D is optimal for lesion dilatation.

FIGS. 16 A-B illustrate cross-lateral views of the in vivo "lesion-length selective" feature of the inflatable member for the FICS LLS PTA Catheter for successive lesion treatment, as an embodiment. In FIG. 16A, a hypothetical vessel 1600A is shown, having a first lesion 1602 and a second lesion 1601. On the right, the inflatable member 1620 of the FICS LLS PTA Catheter can be exposed from the distal end of the FICS Support Catheter 1630, wherein the length of the inflatable member 1620 can be selectively adjusted to the length of the lesion (L1), angiographically verifiable through the distance formed between radiopaque markers 1621 and 1631, the first marker incorporated into a distal inflatable member portion, the second incorporated into a distal support catheter shaft portion, and positioned at either end of the lesion length of the first lesion. The inflated balloon can be controllably dilated along the lesion length by radially exerting pressure perpendicular to the surface of the lesion until the recanalized lesion can be widened substantially to restore luminal patency.

In FIG. 16B, the hypothetical vessel 1600B is shown, wherein the first lesion 1602 has been treated successfully, and the FICS LLS PTA Catheter has been repositioned, with the inflatable member portion shown controllably extended so that the length of the inflatable member 1620 can be aligned with the length of the second lesion 1601 (L2). When the balloon is dilated, the pressure can be radially exerted against the surface of the lesion until patency can be restored in the second lesion. The procedure can be repeated as many times as necessary using the FICS configurations described herein.

4. Dimensional Characteristics of FICS System

To construct therapeutic-specific configurations of the FICS System of the present disclosure, the individual "functional units" and "functional subunits" of the FICS System must be designed so that the dimensional specifications of these components ("FICS specifications") are interoperable over a broad operational range. For example, catheters, PTA balloons, dilators, and guide wires are generally manufactured as set of variable products that provide several sizing options for selecting instrument length and instrument diameter that can cover a broad range of procedural applications. Because the FICS System is intended to provide a comprehensive medical device platform for treating a broad range of complex lesions and CTOs, the dimensional operational range for each critical component of the FICS System components can be determined. The specific interoperability and dimensional specifications for the FICS System components can be described in reference to a hypothetical "FICS CTO Dilator configuration" in FIG. 15, which is described in Examples 1-7 below.

5. Manufacture and Material Selection for FICS

In general, any components of the FICS platform can be constructed by utilizing the methods known to persons skilled in the art. Dilator and/or inflatable members of both Dilator and PTA catheter can be constructed substantially in cylindrical form, having uniformly positioned mantle surfaces along a longitudinal axis, wherein the length sections shaped with a variable tapering profile can be attached to form defined cone regions of the polymeric body/balloon. The dilation elements (polymeric body/balloon) can be located at the distal end of the indwelling FICS catheter during treatment. The inflation can be typically facilitated by incorporating one or more lumens, wherein at least one lumen can be in fluid communication with the elongate, inflatable member, and wherein one or more lumen(s) can facilitate inflation and transport contrast agents and other fluids. FICS PTA Catheter may comprise at least a guide wire lumen and an inflation lumen, provided as dual lumen configurations in side-by-side or coaxial (nested) arrangement. These lumen configurations can be provided as extruded tubing, forming the "inner member," as opposed to the outer member, or catheter shaft. Inner member comprising the one or more lumen and the outer member, or a catheter shaft can be designed to have a fixed length or length adjustability.

All FICS functional units intended for insertion into the SC can be designed to be guidable with a guide wire along the complete length of the instrument, so that the guide wire can enter at the distal tip and exit at the proximal hub. For PTA catheters, such a design can be referred to as an over-the-wire ("OTW") configuration. In contrast to the OTW type of balloon dilation catheters, the rapid exchange (RX) type of balloon dilation catheter instruments can be operated with a significantly shorter guide wire length. Such catheter types can contain a guide wire exit port proximally positioned at a defined distance from the distal tip, so that the guide wire can be contained only within a limited, distally positioned guide wire lumen length or section, and does not need to extend along the complete inner guide wire lumen length. Whereas normal RX ports may be configured as single, annular openings exiting from a proximal position of the GW lumen through the instrument shaft, FICS requires the RX port of insertable functional units to be constructed as a slitted slot maintained over a significant shaft length portion. With respect to the FICS system, the insertable FICS Dilator and PTA catheter components may benefit from an RX port for enabling decreased GW lengths, particularly for systems having a usable length exceeding 150 cm.

The FICS catheter components can be manufactured from biocompatible, polymeric, metallic and ceramic materials. For example, the catheter components may be manufactured from aliphatic, semiaromatic and aromatic polyamides; polyether ether ketones (PEEK); polyimides; linear and nonlinear, branched or nonbranched, low molecular weight, medium molecular weight, or high molecular weight; low density, medium density, or high density polyolefins, including polyethylene and polypropylene, silicones, thermoplastic elastomers, such as polyurethanes (TPEs) and fluoroelastomers, polycarbonates, polyethylene terephthalate (PET) and combinations, including blends and copolymers of any of these materials.

The FICS catheter components can also be fabricated as a single layer, dual-layer, or multi-layer configurations. In the instance of dual-layer or multi-layer configurations, certain catheter elements, including for example the shaft and the balloon, may utilize the same material for each layer or may utilize different materials for each layer. The multiple layers can be glued, melted or fused together with an adhesive or employing a co-extrusion process. Alternatively, the multiple layers are not required to be attached or glued together, instead, the multiple layers may be allowed to move independently. Additionally, the durometer of the material(s) selected for each layer may be altered to further alter the performance aspects of the individual catheter components. Also, the chemical functionality and/or physical polarity of the material can be changed to enhance interfacial adhesion between the differing layers and/or to provide exposed surfaces and/or inner lumen with an increased lubriciousness or changed surface energy when in contact with a guide wire, injected liquids, or functional coatings, for example.

These chemical and physical treatments or alternations/variations may include for instance chemical additives that can introduce another chemical functionality to the interfacial surface, when added to an exemplary base polymer formulation intended to form one or more layers of the catheter component, for example, including functional groups such as carboxy- and/or amino groups, which can effectively enhance the underlying polarity of the layer and the substrate, thus facilitating enhanced adhesion and mechanical fixation strength in between one or more layered structures of catheter components.

Other surface modifications or plasma techniques can be employed for changing the chemical and/or the mechanical properties of the underlying substrate, wherein the plasma modification of the material(s) may affect the polarity and/or the surface energy of the balloon layer(s). Other suitable techniques may incorporate additives, adhesives and/or filling agents, which can introduce other beneficial properties to catheter materials. For example, the catheter shaft or the balloon may incorporate radiopaque elements embedded within polymeric materials to selectively increase fluoroscopic visibility at desired shaft locations. Additionally the shaft may incorporate fluoropolymer-based filler particles/fibers to permanently decrease the frictional coefficient as compared to an untreated base-polymer formulation or activatable, single-use coatings. Furthermore, the shaft can be reinforced and may contain metal or polymer-based strands, fibers, wires, braids, meshes and/or fabrics embedded as layers, sections or regions into the base-shaft material.

The FICS catheter components can be manufactured by following various methods known to persons skilled in the art, including single-, dual-, and or multilayer extrusion, blow molding, dip molding, deposition or other manufacturing methods suitable for manufacturing FICS catheter components. The material for forming FICS catheters may be subjected to mechanical processes before, during or after the catheter manufacture. If an extrusion process is utilized for the manufacturing process, the tubular member for forming the shaft member can be stretched before or during the extrusion process. The temperature, the extrusion pressure, or other parameters can be changed during the manufacturing processes to affect the properties of the manufactured shaft.

EXAMPLES

Example 1

Functional Dimensions of FICS System

Figure 15:
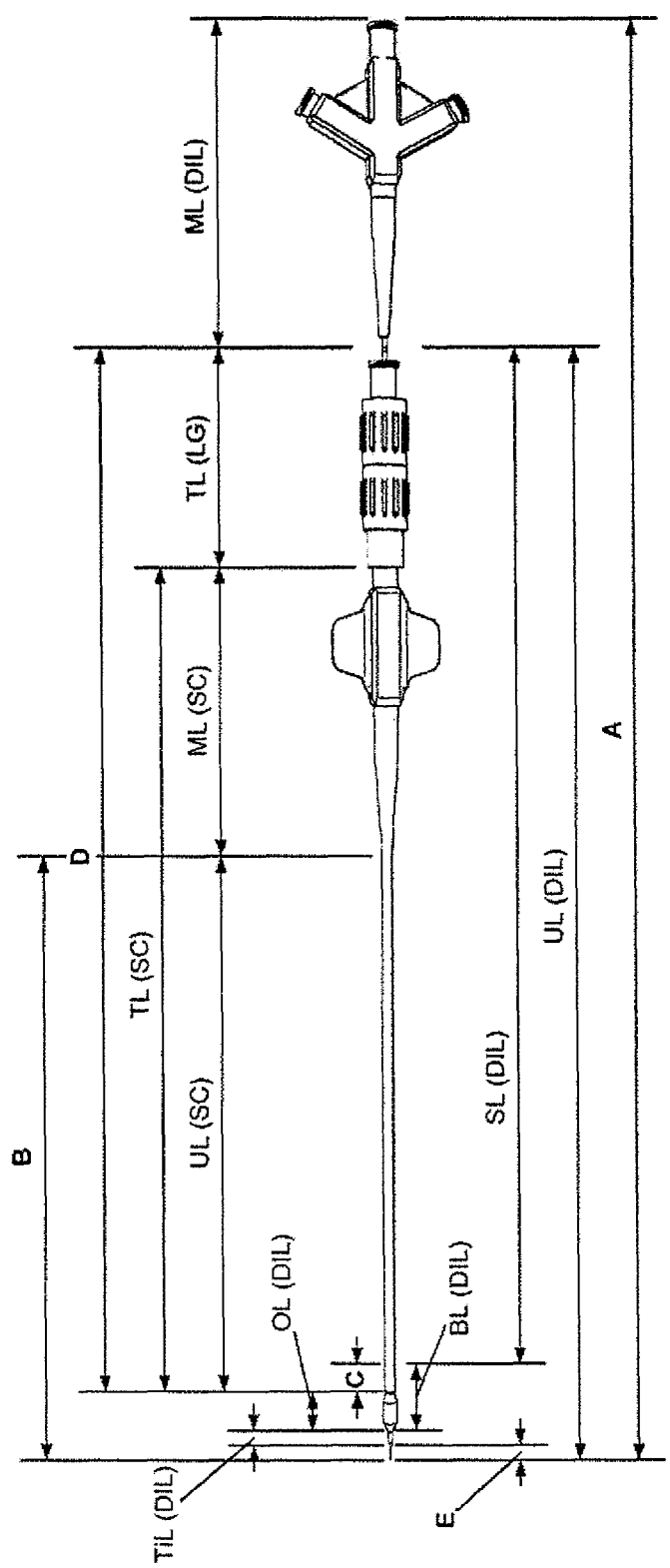
FIG. 15 is a dimensional diagram of a FICS System in a fully extended CTO Dilator configuration, showing the relative dimensional interoperability of the individual "functional units" and "functional subunits" as a convenient reference.

FIG. 15 is a dimensional diagram of a FICS System in a fully extended "CTO Dilator configuration," showing the relative dimensional interoperability of the individual "functional units" and "functional subunits" as a convenient reference. In FIG. 15, the hypothetical dimensional values for the components of the "FICS CTO Dilator configuration" are assigned with both "component-specific reference abbreviations" (LG, SC, PTA, OIL, and CTO) and "functional dimension-specific reference abbreviations" (TL, UL, ML, RL, BL, OL, SL, TiL). The "functional dimension-specific reference abbreviations" represent the respective lengths of the FICS components, as provided in Table 1 under Example 1. Furthermore, Table 2 provides respective formulas for calculating the "functional dimensions" corresponding to the respective components (labeled in FIG. 15; listed in Table 1), wherein the various "functional dimensions" listed in the first column of Table 2 represent the operational lengths and operational relationships among the components of the "functional units" and "functional subunits."

In FIG. 15, the functional dimension "A" refers to the variable total length TL of the FICS System, the functional dimension "B" refers to the variable usable length portion UL; the functional dimension "D" refers to the fixed total length portion of the combined total lengths of the Support Catheter SC and the Lock Grip LG; and the functional dimension "C" refers to a variably recessed length portion (describing the sheathed balloon length portion RL relative to the complete balloon length portion BL). The difference BL-RL defines the operational balloon length OL that can be variably adjusted between minimum and maximum thresholds wherein the adjustable operational length is measured as the distance between the position of the radiopaque markers incorporated into the distal end of the balloon member of the PTA catheter and the position of the radiopaque markers incorporated into the distal end of the support catheter shaft. Functional dimension "E" refers to the variable length of the "CTO Penetration Tip."

TABLE 1

ABBREVIATIONS FOR FICS COMPONENTS

| | |
|---|---|
| TL | Total Length |
| UL | Usable Length |
| ML | Manifold Length |
| RL | Recessed Length |
| BL | Balloon Length |
| OL | Operational Balloon Length |
| SL | Shaft Length |
| TiL | Tip Length |
| (LG) | Lock Grip |
| (SC) | Support Catheter |
| (PTA) | PTA Catheter |
| (DIL) | Dilator |
| (CTO) | CTO Penetration Tip |

TABLE 2

CALCULATION OF FUNCTIONAL DIMENSIONS

| Functional Dimensions | EXEMPLARY CORRELATIONS (CTO Dilator Configuration) | |
|---|---|---|
| A | TL (DIL) = UL (DIL) + ML (DIL) | (variable) |
| B | UL (DIL) = TI(LG) + ML(SC) + UL (SC) + OL (DIL) + TiL (DIL) + TiL (CTO) | (variable) |
| C | D − SL (DIL) = RL (DIL) = BL (DIL) − OL (DIL) | (variable) |
| D | TL (SC) + TL (LG) = UL (SC) + ML (SC) + TL (LG) | (constant) |
| E | TiL(CTO) | (variable) |
| ΔB | B (max) − B (min) = │ΔB│ = │ΔC│ + │ΔE│<br>OL (max) = BL − C (min)<br>OL (min) = BL − C (max) | UL Range |
| ΔC | C (max) − C (min) | RL Range |
| ΔE | E (max) − E (min) | CTO Penetration Range |
| Other UL: | UL (PTA) = UL (SC) + OL (PTA) + TiL (PTA)<br>UL (REENTRY) = UL (SC) + TiL (Dil) + OL (REENTRY) | |

Example 2

FICS Total Length TL(A)

The "Total Length" (TL) refers to the total length of the FICS System or individual functional units. The Total Length (TL) can be derived by adding together the respective lengths of the components for the functional units and functional subunits. The relative correlations between the lengths of components for the "CTO Dilator configuration" are provided in TABLE 2, as an example. Exemplary total length (TL) ranges for the respective components of the FICS System are provided in TABLE 3 (CTO Dilator configuration) and in TABLE 4 (LLS PTA Configuration) under Example 3 below. The TL of the "FICS Reentry" and/or "FICS LLS PTA" configuration can be derived similarly (not shown). Since the TL of the "FICS LLS PTA configuration" will always exceed the TL of the "CTO Dilator" and/or "Reentry Dilator" configuration, the TL of the FICS LLS PTA configuration can be utilized by the physician for adequate GW length selection prior to commencing the procedure.

Example 3

FICS Usable Length UL (B)

The "Usable Length" (UL) refers to the indwelling/working length portion of the FICS System or the individual functional units. The UL correlates with the distance between the access point (patient entry site) and the target-treatment point that can be reached by the FICS System. The FICS System can provide a range of different, predefined ULs corresponding to the respective components of the FICS System for treating a broad range of complex lesions and/or CTOs. As examples, the usable lengths of respective components are provided for two therapeutic-specific configurations: (a) the FICS CTO Dilator configuration (TABLE 3); and (b) the FICS LLS PTA Configuration (TABLE 4). Clinically relevant access lengths correlating with the distance measurable from the most commonly used (predefined) patient entry points to a hypothetical target site (distance beyond a hypothetical lesion located in a predefined target region) are provided in TABLE 5. The usable length UL portion of the components of the FICS System can be selected based on the determined access length.

It can be shown, in absolute values, that the usable length portion "B" of the FICS system in the "CTO Dilator configuration" with an integrated CTO penetration tip can be adjusted in a dimensional range │ΔB│ that is equivalent to the combined balloon and CTO tip extension range │ΔC│+│ΔE│, wherein the operational balloon length and the CTO penetration depth can be varied independently with respect to the other. This leads to a variable adjustability of both usable length "B" as well as total length "A" of the FICS System, and this differs in comparison to conventional systems, wherein both usable length and total length are constant. Due to this specific configuration, the FICS system in the "CTO Dilator configuration" enables a custom length-adjustable operational balloon length that can be adapted for "lesion-length selective" anchoring, wherein the system itself can exhibit an adjustable UL portion substantially at the same time.

Other FICS system configurations, such as the "FICS Reentry Dilator configuration" or the "FICS LLS PTA configuration" can exhibit variable usable length ranges, as described in TABLE 2. In the case of the FICS LLS PTA configuration, the operational CTO tip length may be omitted to arrive at analogous dimensional correlations referenced in TABLE 4.

TABLE 3

FICS CTO DILATOR CONFIGURATION

| UL (SYSTEM) = UL (SC) | 800 | | |
|---|---|---|---|
| all units [mm] | Min | Max | Opt |
| ML (SC) | 10 | 50 | 20 |
| TL (LG) | 20 | 100 | 50 |
| TiL (DIL) | 5 | 10 | 5 |
| TiL (CTO) | 0 | 10 | 0-10 |
| OL (DIL) | 0 | 180 | 0-180 |
| ML (DIL) | 40 | 80 | 80 |
| TL (SYSTEM) = TL (DIL) | 875 | 1230 | 1135-1145 |
| BL (DIL) | 10 | 200 | 200 |
| RL (DIL) | 10 | 20 | 20 |
| SL (DIL) | 820 | 940 | 860 |
| UL (DIL) | 825 | 1140 | 1055 |

TABLE 4

| FICS LLS PTA CATHETER CONFIGURATION | | | |
|---|---|---|---|
| UL (SYSTEM) = UL (SC) | 1350 | | |
| all units [mm] | Min | Max | Opt |
| ML (SC) | 10 | 50 | 20 |
| TL (LG) | 20 | 100 | 50 |
| TiL (PTA) | 5 | 10 | 5 |
| OL (PTA) | 0 | 180 | 0-180 |
| ML (PTA) | 40 | 80 | 80 |
| TL (SYSTEM) = TL (PTA) | 1425 | 1770 | 1685 |
| BL (PTA) | 10 | 200 | 200 |
| RL (PTA) | 10 | 20 | 20 |
| SL (PTA) | 1370 | 1480 | 1400 |
| UL (PTA) | 1385 | 1690 | 1605 |

TABLE 5

| ACCESS LENGTHS (across Lesion) | | | | |
|---|---|---|---|---|
| all units [cm] | Entry Points | | | |
| Target Regions | CFA ipsilateral | CFA contralateral | Brachial | Radial |
| Illiac | 1-30 | 30-60 | 70-100 | 100-130 |
| SFA | 1-30 | 30-60 | 100-130 | 130-160 |
| BTK | 50-80 | 80-110 | 150-180 | 180-210 |

CFA = common femoral artery
SFA = superficial femoral artery
BTK = below the knee Example 4

FICS Compatibility with Guide Wire Length

The TL correlates with the GW length needed to effectively operate all combined functional units in their respective configurations (on/over the guide wire). When planning an interventional procedure, the physician can use the total system length as an orientation for selecting an adequately sized guide wire. TABLE 6 provides a list of recommended and calculated GW lengths correlating with the FICS total length (LLS PTA configuration).

TABLE 6

| FICS GUIDEWIRE LENGTH COMPATIBILITY | | | |
|---|---|---|---|
| GW LENGTH COMPATIBILITY | | TOTAL LENGTH (A) | USABLE LENGTH (B) |
| (recommended) | (calculated)* | all units [mm] | |
| 4500 | 4370 | 2135 | 1800 |
| 4000 | 3970 | 1935 | 1600 |
| 3800 | 3770 | 1835 | 1500 |
| 3500 | 3470 | 1685 | 1350 |
| 3200 | 3170 | 1535 | 1200 |
| 2800 | 2770 | 1335 | 1000 |
| 2600 | 2570 | 1235 | 900 |
| 2400 | 2370 | 1135 | 800 |
| 2000 | 1970 | 935 | 600 |

*GW LENGTH COMPATIBILITY = [(SYSTEM TL (MAX) * 2) + 100]

Example 5

FICS GW Diameter Compatibility ("Guidewire Compatibility")

The "guide wire compatibility" refers to the minimum inner diameter (ID) of the lumen of a functional unit/instrument for passing a guidewire of certain outer diameter without resistance. Guide wire compatibility is governed by the GW lumen ID of each insertable functional unit, for example, the (GW lumen) ID of the Dilator, the PTA catheter, or respectively the lumen ID of the hypotube coaxially embedded into the dilator tip design as utilized in the "CTO Dilator" and/or "Reentry Dilator" configuration. Guide wires can typically be offered with outer diameter ranges between 0.014-0.035 [in], equivalent to 0.356-0.889 [mm]. The functional units of the FICS, particularly the PTA catheter, dilator and hypotube component can be configured to be 0.018 in./0.457 mm compatible. Other dimensions and ranges can be contemplated for different clinical applications.

Example 6

FICS Introducer Sheath Compatibility

The term "Sheath Compatibility" refers to the maximum instrument outer diameter (OD) along the UL that can be introduced through an introducer sheath of commensurate inner diameter without resistance. The components of the FICS System can be dimensionally configured based on the relative diameters of the components. The FICs system can be designed to pass through the inner diameter of introducer sheaths having a variable range. Thus the outer diameter along the usable length portion of the FICS system can be configured to be receivable through an introducer sheath having a compatible inner diameter. For example, TABLE 7 provides the dimensions of a PTA balloon member (widths and lengths) that may be recommended for obtaining sheath compatibility suitable for the FICS LLS PTA configuration, wherein the PTA catheters having balloon diameters that can range between 2.0-7.0 mm, for example. The operational balloon length OL (Table 7) can be adjusted through the interoperation of the SC, the LG and the PTA functional units as described in FIG. 12. The balloon length BL of the Dilator and the PTA catheter can be configured within a fixed range as described in TABLES 3-4. Other dimensions and ranges can be contemplated for different clinical applications. For example, a system for retrograde pedal/tibial access can be dimensioned using a sheath compatible at 3 Fr. For the FICS CTO Dilator configuration, the proximal maximum outer diameter of a polymeric tip (e.g., refer to FIGS. 6-7, components 620/720) can correspond to the minimum inner diameter of the lumen of FICS Support Catheter, for example, ranging between 3.0-4.0 Fr.

TABLE 7

| FICS SHEATH COMPATIBILITY | | | | | | | | |
|---|---|---|---|---|---|---|---|---|
| | Operational Balloon Length [mm] | | | | | | | |
| Balloon Diameter [mm] | 20 | 40 | 60 | 80 | 100 | 120 | 150 | 180 |
| 2.0 | 4Fr | 4Fr | 4Fr | 4Fr | 4Fr | 4Fr | 4Fr | 4Fr |
| 2.5 | 4Fr | 4Fr | 4Fr | 4Fr | 4Fr | 4Fr | 4Fr | 4Fr |
| 3.0 | 4Fr | 4Fr | 4Fr | 4Fr | 4Fr | 4Fr | 4Fr | 4Fr |
| 3.5 | 4Fr | 4Fr | 4Fr | 4Fr | 4Fr | 4Fr | 4Fr | 4Fr |

TABLE 7-continued

FICS SHEATH COMPATIBILITY

| Balloon Diameter [mm] | Operational Balloon Length [mm] | | | | | | | |
|---|---|---|---|---|---|---|---|---|
| | 20 | 40 | 60 | 80 | 100 | 120 | 150 | 180 |
| 4.0 | 5Fr | 5Fr | 5Fr | 5Fr | 5Fr | 5Fr | 5Fr | 5Fr |
| 5.0 | 5Fr | 5Fr | 5Fr | 5Fr | 5Fr | 5Fr | 5Fr | 5Fr |
| 6.0 | 5Fr | 5Fr | 5Fr | 5Fr | 5Fr | 5Fr | 5Fr | 5Fr |
| 7.0 | 5Fr | 5Fr | 5Fr | 5Fr | 5Fr | 5Fr | 5Fr | 5Fr |

Note:
1 [Fr] = 0.333 [mm]

The foregoing description, for purposes of explanation, refers to specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and practical applications, to thereby enable others skilled in the art to best utilize the invention and various embodiments with various modifications as suitable for the particular uses contemplated. It is intended that the scope of the invention be defined by the following claims and their equivalent.

We claim:

1. A catheter system comprising:
multiple shaft-based components, including
one or more support catheters that each includes a support-catheter shaft member with a central lumen, a support-catheter manifold that provides fluid communication to the central lumen, and a support-catheter connector,
one or more dilators that each includes a dilator tip, a dilator shaft member with one or more lumens, a dilator manifold that provides fluid communication to one or more of the one or more lumens, a dilator connector, and a hydraulic chamber that enables hydraulic actuation of the dilator tip, the dilator shaft member having an external diameter that allows the dilator shaft member to be inserted into the central lumen of each of the one or more support catheters, and
one or more percutaneous transluminal angioplasty ("PTA") catheters that each includes an inflatable member attached to a PTA-catheter shaft member with two or more lumens, a PTA-catheter manifold that provides fluid communication to one or more of the two or more lumens, and a PTA-catheter connector, the PTA-catheter shaft member having an external diameter that allows the PTA-catheter shaft member to be inserted into the central lumen of each of the one or more support catheters;
a lock-grip handle that includes a second connector that is complementary to the support-catheter connector, the dilator connector, and the PTA-catheter connector, a lock-grip body, and a first connector complementary to the second connector, the lock-grip handle providing a seal to inhibit fluid communication to an enclosed volume between an inner surface of a lumen of a first shaft-based component, selected from the multiple shaft-based components connected to the second connector and an external surface of a second shaft-based component, selected from the multiple shaft-based components, inserted through the first connector and into the lumen of the first shaft-based component; and
a steering hub that includes a second steering-hub connector that is complementary to the support-catheter connector, the dilator connector, and the PTA-catheter connector, a first steering-hub connector complementary to the second steering-hub connector, and a steering-hub body that provides control features that, when manipulated, translate and rotate the dilator tip connected by elastomeric tubing to the steering hub.

2. The catheter system of claim 1 wherein the multiple shaft-based components and the lock-grip handle are assembled to form multiple different multi-component catheters, including:
a first multi-component catheter comprising a support catheter, selected from the one or more support catheters, connected to the second connector of the lock-grip handle, through the first connector of which a dilator shaft member, selected from the one or more dilators, is inserted in order to extend into the central lumen of the support catheter;
a second multi-component catheter comprising a support catheter, selected from the one or more support catheters, connected to the second connector of the lock-grip handle, through the first connector of which a dilator shaft member, selected from the one or more dilators, is inserted in order to extend into the central lumen of the support catheter, the dilator connector connected to the second steering-hub connector of the steering hub; and
a third multi-component catheter comprising a support catheter, selected from the one or more support catheters, connected to the second connector of the lock-grip handle, through the first connector of which a PTA-catheter shaft member, selected from the one or more PTA catheters, is inserted in order to extend into the central lumen of the support catheter.

3. The catheter system of claim 1 wherein the one or more support catheters include at least one support catheter with the support-catheter shaft member having a first end and a second end, the first end of the support-catheter shaft member connected to a second end of the support-catheter manifold, and the second end of the support-catheter shaft member having a circular edge, the plane of which is orthogonal to a long axis of the central lumen of the at least one support catheter.

4. The catheter system of claim 3 wherein the support-catheter connector comprises a female luer lock mounted at a first end of the support-catheter manifold.

5. The catheter system of claim 3 wherein the support-catheter manifold includes one or more flushing ports through which fluids are introduced into the central lumen of the at least one support catheter.

6. The catheter system of claim 3 wherein the support-catheter shaft member includes one or more radiopaque markers.

7. The catheter system of claim 1 wherein the multiple shaft-based components include at least one dilator, selected from the one or more dilators, with the dilator shaft member having a first end and a second end, the first end of the dilator shaft member connected to a second end of the dilator manifold and the second end of the dilator shaft member containing a steerable hydraulically actuated dilator tip.

8. The catheter system of claim 7 wherein the at least one dilator includes an actuation lumen that introduces hydraulic fluid into the hydraulic chamber in which a portion of the dilator tip is slidably and sealably contained.

9. The catheter system of claim 8 wherein the at least one dilator additionally includes an inflation lumen that inflates an anchoring member positioned between the second end of the dilator shaft member and the dilator tip.

10. The catheter system of claim 8 wherein the at least one dilator additionally contains an elastomeric tube that interconnects the steerable hydraulically actuated dilator tip with the steering hub.

11. The catheter system of claim 10 wherein the at least one dilator additionally includes an inflation lumen that inflates an anchoring member positioned between the second end of the dilator shaft member and the dilator tip.

12. The catheter system of claim 7 wherein the dilator connector comprises a female luer lock mounted at a first end of the dilator manifold.

13. The catheter system of claim 7 wherein the dilator shaft member includes one or more radiopaque markers.

14. The catheter system of claim 1 wherein the multiple shaft-based components include at least one PTA catheter, selected from the one or more PTA catheters, with the PTA-catheter shaft member having a first end and a second end, the first end of the PTA-catheter shaft member connected to a second end of the PTA-catheter manifold, and the second end of the PTA-catheter shaft member connected to the inflatable member so that, when the PTA-catheter shaft member lies within the central lumen of a support-catheter selected from the one or more support catheters, a length of the inflatable member that lies beyond an end of the central lumen of a support catheter selected from the one or more support catheters is varied by translating the PTA-catheter shaft member with respect to the support-catheter shaft member.

15. The catheter system of claim 14 wherein the PTA-catheter shaft member includes one or more radiopaque markers.

16. The catheter system of claim 1 wherein the lock-grip handle provides features that, when manipulated,
fix the relative positions of a first shaft-based component, selected from among the multiple shaft-based components, connected to the second connector of the lock-grip handle and a second shaft-based component, selected from among the multiple shaft-based components, inserted through the first connector and into a lumen of the first shaft-based component;
unfix the relative positions of the first shaft-based component connected to the second connector of the lock-grip handle and the second shaft-based component inserted through the first connector and into a lumen of the first shaft-based component; and
controllably advance and retract the second shaft-based component, inserted through the first connector and into a lumen of the first shaft-based component connected to the second connector of the lock-trip handle, with respect to the first shaft-based component.

17. A catheter system comprising:
multiple shaft-based components, including
one or more support catheters, each including a support-catheter connector,
one or more dilators, each including a dilator connector, a dilator tip, and a hydraulic chamber that enables hydraulic actuation of the dilator tip, and
one or more percutaneous transluminal angioplasty ("PTA") catheters, each including a PTA-catheter connector;
a lock-grip handle that includes a second lock-grip connector that is complementary to the support-catheter connector, the dilator connector, and the PTA-catheter connector, a lock-grip body, and a first lock-grip connector complementary to the second lock grip connector, the lock-grip handle providing a seal to inhibit fluid communication to an enclosed volume between an inner surface of a lumen of a first shaft-based component, selected from among the multiple shaft-based components, connected to the second lock-grip connector and an external surface of a second shaft-based component, selected from among the multiple shaft-based components, inserted through the first lock-grip connector and into the lumen of the first shaft-based component; and
a steering hub that includes a second steering-hub connector that is complementary to the support-catheter connector, the dilator connector, and the PTA-catheter connector, a first steering-hub connector complementary to the second steering-hub connector, and a steering-hub body that provides control features that, when manipulated, translate and rotate the dilator tip connected by elastomeric tubing to the steering hub.

18. The catheter system of claim 17 wherein the steering hub further comprises:
a first casing member, having the first steering-hub connector at a first end and a shaft with protrusions at a second end, to which the elastomeric tubing is attached; and
a second casing member with a cylindrical bore opening to a first end and a second end that includes the second steering-hub connector and a central, hollow protrusion through which the elastomeric tubing passes, the cylindrical bore containing features complementary to the protrusions of the shaft of the first casing member.

19. The catheter system of claim 18 wherein the first casing member is manipulated to rotate within the cylindrical bore of the second casing member, imparting a rotation to a steerable dilator tip at an end of a dilator and connected to the elastomeric tubing.

20. The catheter system of claim 18 wherein the first casing member is manipulated to translate within the cylindrical bore of the second casing member, imparting a translation to either a steerable dilator tip at an end of a dilator and connected to the elastomeric tubing.

21. The catheter system of claim 18 wherein the first casing member occupies one of multiple rotational positions and one of multiple translational positions determined by the protrusions of the shaft and features complementary to the shaft protrusions.

\* \* \* \* \*